United States Patent
Tamura et al.

(10) Patent No.: US 6,333,080 B1
(45) Date of Patent: *Dec. 25, 2001

(54) LIQUID-CRYSTAL ALKENYLTOLAN DERIVATIVE, LIQUID-CRYSTAL COMPOSITION, AND LIQUID-CRYSTAL DISPLAY ELEMENT

(75) Inventors: Norio Tamura; Atsuko Fujita; Shuichi Matsui; Kazutoshi Miyazawa, all of Chiba; Norihisa Hachiya, Saitama; Etsuo Nakagawa, Chiba, all of (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,554

(22) PCT Filed: Aug. 18, 1997

(86) PCT No.: PCT/JP97/02849

§ 371 Date: May 6, 1999

§ 102(e) Date: May 6, 1999

(87) PCT Pub. No.: WO98/07672

PCT Pub. Date: Feb. 26, 1998

(30) Foreign Application Priority Data

Aug. 20, 1996 (JP) .................................................. 8-218879

(51) Int. Cl.$^7$ .......................... C09K 19/34; C09K 19/20; C09K 19/30; C07C 25/13; C07C 43/00; C07D 239/02

(52) U.S. Cl. ................ 428/1.1; 252/299.01; 252/299.61; 252/299.63; 252/299.66; 570/127; 570/129; 570/130; 568/583; 568/585; 568/588; 568/631; 568/634; 544/298; 544/335

(58) Field of Search .................. 252/299.01, 299.61, 252/299.63, 299.66; 428/1.1; 570/127, 129, 130; 544/298, 335; 568/583, 585, 588, 631, 634

(56) References Cited

U.S. PATENT DOCUMENTS

| 5,399,292 | * | 3/1995 | Buchecker et al. | 252/299.63 |
| 5,776,367 | * | 7/1998 | Matsui et al. | 252/299.63 |
| 6,063,456 | * | 5/2000 | Hirschmann et al. | 428/1.1 |

FOREIGN PATENT DOCUMENTS

| 3-58944 | 3/1991 | (JP) . |
| 3-176437 | 7/1991 | (JP) . |
| 5-65236 | 3/1993 | (JP) . |
| 5-310619 | 11/1993 | (JP) . |
| 6-192143 | 7/1994 | (JP) . |
| 8-73381 | 3/1996 | (JP) . |

* cited by examiner

*Primary Examiner*—Shean C. Wu
(74) *Attorney, Agent, or Firm*—McDermott, Will & Emery

(57) ABSTRACT

A liquid crystalline alkenyltolan derivative expressed by the general formula $$C_tH_{2t-1}-G-(CH_2)_m-A_1-B_1-(A_2-B_2)_n-(A_3-B_3)_p-A_4-X$$

wherein $A_1$, $A_2$, $A_3$, and $A_4$ independently represent a 1,4-cyclohexylene, 1,4-phenylene in which one or two hydrogen atoms may be replaced by a fluorine atom(s), dioxane-2,5-diyl, or pyrimidine-2,5-diyl group; $B_1$, $B_2$, and $B_3$ independently represent a covalent bond, an 1,2-ethylene, 1,2-ethenylene, 1,2-ethynylene, oxymethylene, methylenoxy, carbonyloxy, or 1,4-butylene group provided that at least one of $B_1$, $B_2$, and $B_3$ represents an 1,2-ethynylene group; G represents a covalent bond or an oxygen atom; $C_tH_{2t-1}$ represents an alkenyl group having t carbon atoms; n and p are each 0 or 1; and X represents an alkyl group having 1 to 10 carbon atoms. The derivative provides a liquid-crystal compound and a liquid-crystal composition which have high anisotropy, high elastic constant ratio, excellent comparability with other liquid-crystal compounds, and low viscosity and are chemically and physically stable.

32 Claims, No Drawings

LIQUID-CRYSTAL ALKENYLTOLAN DERIVATIVE, LIQUID-CRYSTAL COMPOSITION, AND LIQUID-CRYSTAL DISPLAY ELEMENT

TECHNICAL FIELD

Present invention relates to a tolan derivative, novel liquid crystalline compounds exhibiting useful physical properties; to liquid crystal compositions comprising the derivative and exhibiting useful physical properties; and to liquid crystal display devices including the liquid crystal composition.

BACKGROUND ART

Liquid crystal display devices utilize optical anisotropy and dielectric anisotropy of liquid crystalline compounds. As display mode of the devices, twisted nematic (TN) mode, super twisted nematic (STN) mode, dynamic scattering (DS) mode, guest-host (GH) mode, and DAP (Deformation of Aligned Phases) mode have been known. As driving mode for the display devices, static driving mode, time shearing addressing mode, active matrix driving mode, and two-frequency addressing mode have been known.

Liquid crystal compositions used for these liquid crystal display devices are required to exhibit liquid crystal phase at wide temperature range and to be stable against heat, light, moisture, air, electric field, and electromagnetic radiation. Accordingly, several kind of liquid crystal compounds are used in combination for display device materials. Sometimes, number of the liquid crystal compounds becomes more than 20 and therefore each of the liquid crystal compounds is required to be good in miscibility with other liquid crystal compounds. Particularly, since the display devices have recently come to be used in severe environments, improvement of miscibility at low temperatures has come to be required. Besides, in keeping with demand for display devices of higher qualities, improvements of liquid crystal compositions in the speed for responding to the change of electric field and in the steepness are required, and thus it has become necessary to control physical properties such as dielectric anisotropy and ratio of elastic constants to most suitable values depending on the display mode and the shape of the devices.

Another characteristic required of effective liquid crystal display devices is that the devices have a good display contrast and wide viewing angle. For this purpose, it is necessary to keep the product ($\Delta n \cdot d$) of optical anisotropy ($\Delta n$) multiplied by cell thickness (d) at a constant value. One method for increasing the response speed is to reduce the cell thickness (d). Accordingly, in order to achieve this purpose while maintaining the product ($\Delta n \cdot d$) described above at a desired value, liquid crystal compositions having high $\Delta n$ are necessary and in order to produce such liquid crystal compositions, liquid crystalline compounds having high $\Delta n$ become necessary.

As compounds having comparatively high $\Delta n$, tolan compounds expressed by the general formula (10) are disclosed in Laid-open Japanese Patent Publication No. Sho 61-5031, alkynyloxytolan compounds expressed by the general formula (11) are disclosed in Laid-open Japanese Patent Publication No. Hei 2-207056, alkynyltolan compounds expressed by the general formula (12) are disclosed in Laid-open Japanese Patent Publication No. Hei 2-180840, allylcyclohexyltolan compounds expressed by the general formula (13) are disclosed in Laid-open Japanese Patent Publication No. Hei 3-58944, and fluorotolan type alkenyl compounds expressed by the general formula (14) are disclosed in Laid-open Japanese Patent Publication No. Hei 5-65236, respectively.

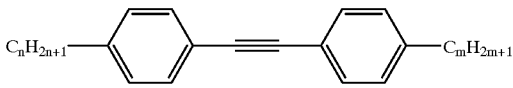

(10)

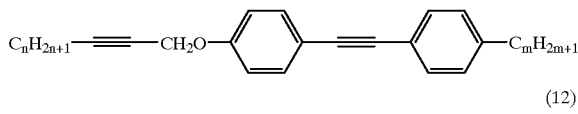

(11)

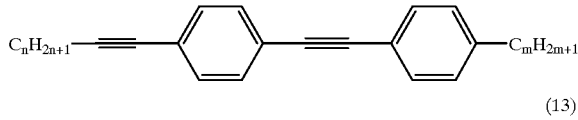

(12)

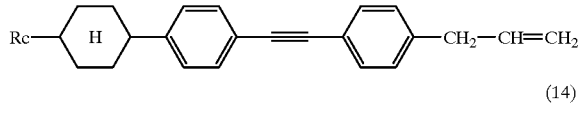

(13)

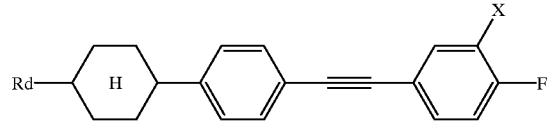

(14)

wherein Rc represents an alkyl group having 1 to 8 carbon atoms,

Rd represents an alkenyl group having 2 to 14 carbon atoms, and

X represents H or F.

However, the compounds expressed by the general formula (10) are not sufficiently high in $\Delta n$ and dielectric anisotropy, and the compounds expressed by the general formula (11) or (12) have such defects that the viscosity of the compounds is high since they have triple bond at a lateral chain and the compounds are poor in miscibility. With respect to the compounds expressed by the general formula (13), data indicating their liquid crystallinity are not shown. Further, with respect to the compounds expressed by the general formula (14), whereas a fluorine atom(s) is introduced into a benzene ring, the increase of the value of $\Delta n$ is not sufficient.

DISCLOSURE OF THE INVENTION

An object of the present invention is to provide novel liquid crystal compounds compensating the defects in the prior art, that is, tolan derivatives which are novel liquid crystalline compounds having a sufficiently high $\Delta n$, high dielectric anisotropy, large ratio of elastic constants, excellent miscibility with other liquid crystal compounds, and low viscosity, and being chemically and physically stable. Another object of the present invention is to provide liquid crystal compositions comprising the tolan derivative, and to provide liquid crystal display devices including the liquid crystal composition.

As a result of the investigation by the present inventors to solve the problems described above, compounds having a novel structure, and exhibiting improved characteristics compared with known liquid crystalline compounds have been found to accomplish the present invention.

The present invention is summarized as follows:
(1) A liquid crystalline alkenyltolan derivative expressed by the general formula (1)

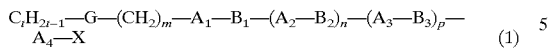

(1)

wherein $A_1$, $A_2$, $A_3$, and $A_4$ independently represent a 1,4-cyclohexylene, 1,4-phenylene in which one or two hydrogen atoms may be replaced by a fluorine atom(s), dioxane-2,5-diyl, or pyrimidine-2,5-diyl group; $B_1$, $B_2$, and $B_3$ independently represent a covalent bond, an 1,2-ethylene, 1,2-ethenylene, 1,2-ethynylene, oxymethylene, methylenoxy, carbonyloxy, or 1,4-butylene group provided that at least one of $B_1$, $B_2$, and $B_3$ represents an 1,2-ethynylene group; G represents a covalent bond or an oxygen atom; $C_tH_{2t-1}$ represents an alkenyl group having t carbon atoms wherein t is an integer of 2 to 10; m is an integer of 0 to 2; n and p are independently an integer of 0 or 1; X represents an alkyl group having 1 to 10 carbon atoms, a fluoroalkyl group having 1 to 10 carbon atoms, a chlorine atom, a bromine atom, or a cyano group wherein one or more methylene groups or fluoromethylene groups in the alkyl group or the fluoroalkyl group may be replaced by an oxygen atom(s) or an 1,2-ethenylene group, but adjacent two methylene groups should not be simultaneously replaced by them; provided that when $A_4$ represents 1,4-phenylene group which is not substituted with a fluorine atom(s), there is no case that G represents a covalent bond and t+m=3 simultaneously; and each element in the molecule may be its isotope.
(2) The liquid crystalline alkenyltolan derivative recited in paragraph (1) above wherein n and p are 0.
(3) The liquid crystalline alkenyltolan derivative recited in paragraph (1) above wherein n is 1 and p is 0.
(4) The liquid crystalline alkenyltolan derivative recited in paragraph (1) above wherein n and p are 1.
(5) The liquid crystalline alkenyltolan derivative recited in paragraph (2) above wherein X represents a chlorine atom, a bromine atom, a cyano group, or a fluoroalkyl group having 1 to 10 carbon atoms in which one or more fluoromethylene groups may be replaced by an oxygen atom(s) or 1,2-ethenylene group(s).
(6) The liquid crystalline alkenyltolan derivative recited in paragraph (2) above wherein X represents an alkyl group having 1 to 10 carbon atoms in which one or more methylene groups may be replaced by an oxygen atom(s) or an 1,2-ethenylene group(s); and $A_1$ and $A_4$ independently represent a 1,4-phenylene group in which one or two hydrogen atoms may be replaced by a fluorine atom(s)
(7) The liquid crystalline alkenyltolan derivative recited in paragraph (2) above wherein G represents a covalent bond, t+m=4, and a double bond exists at a terminal of the molecule.
(8) The liquid crystalline alkenyltolan derivative recited in paragraph (2) above wherein G represents a covalent bond, t+m=5, and a double bond exists at a second position counting from a terminal of the molecule.
(9) The liquid crystalline alkenyltolan derivative recited in paragraph (3) above wherein X represents a chlorine atom, a bromine atom, a cyano group, or a fluoroalkyl group having 1 to 10 carbon atoms in which one or more fluoromethylene groups may be replaced by an oxygen atom(s) or an 1,2-ethenylene group(s).
(10) The liquid crystalline alkenyltolan derivative recited in paragraph (3) above wherein X represents an alkyl group having 1 to 10 carbon atoms in which one or more methylene groups may be replaced by an oxygen atom(s) or an 1,2-ethenylene group(s).
(11) The liquid crystalline alkenyltolan derivative recited in paragraph (10) wherein G represents a covalent bond, t+m=4, and a double bond exists at a terminal of the molecule.
(12) The liquid crystalline alkenyltolan derivative recited in paragraph (10) wherein G represents a covalent bond, t+m=5, and a double bond exists at a second position counting from a terminal of the molecule.
(13) The liquid crystalline alkenyltolan derivative recited in paragraph (11) wherein $B_1$ represents a covalent bond and $B_2$ represents an 1,2-ethynylene group.
(14) The liquid crystalline alkenyltolan derivative recited in paragraph (12) wherein $B_1$ represents a covalent bond and $B_2$ represents an 1,2-ethynylene group.
(15) The liquid crystalline alkenyltolan derivative recited in paragraph (13) wherein $A_1$ represents an 1,4-cyclohexylene group, and $A_2$ and/or $A_4$ represents an 1,4-phenylene group in which a hydrogen atom(s) may be replaced by a fluorine atom(s).
(16) The liquid crystalline alkenyltolan derivative recited in paragraph (15) above wherein $A_2$ and $A_4$ represent 1,4-phenylene group in which a hydrogen atom(s) is not replaced by a fluorine atom(s).
(17) The liquid crystalline alkenyltolan derivative recited in paragraph (15) above wherein $A_2$ represents 1,4-phenylene group in which two hydrogen atoms are replaced by fluorine atoms and $A_4$ represents 1,4-phenylene group in which a hydrogen atom(s) is not replaced by a fluorine atom(s).
(18) The liquid crystalline alkenyltolan derivative recited in paragraph (3) above wherein G represents a covalent bond, t+m=4, and a double bond exists at a terminal of the molecule.
(19) The liquid crystalline alkenyltolan derivative recited in paragraph (3) above wherein G represents a covalent bond, t+m=5, and a double bond exists at a second position counting from a terminal of the molecule.
(20) The liquid crystalline alkenyltolan derivative recited in paragraph (4) above wherein X represents a chlorine atom, a bromine atom, a cyano group, or a fluoroalkyl group having 1 to 10 carbon atoms in which one or more fluoromethylene groups may be replaced by an oxygen atom(s) or an 1,2-ethenylene group(s).
(21) The liquid crystalline alkenyltolan derivative recited in paragraph (4) above wherein X represents an alkyl group having 1 to 10 carbon atoms in which one or more methylene groups may be replaced by an oxygen atom(s) or an 1,2-ethenylene group(s).
(22) The liquid crystalline alkenyltolan derivative recited in paragraph (21) above wherein $A_2$ and/or $A_4$ represents 1,4-phenylene group in which one or two hydrogen atoms may be replaced by a fluorine atom(s) and $B_3$ represents 1,2-ethynylene group.
(23) The liquid crystalline alkenyltolan derivative recited in paragraph (21) above wherein $A_2$ and/or $A_3$ represents an 1,4-phenylene group in which one or two hydrogen atoms may be replaced by an fluorine atom(s) and $B_2$ represents an 1,2-ethynylene group.
(24) The liquid crystalline alkenyltolan derivative recited in paragraph (23) above wherein one or two hydrogen atoms of $A_2$ and/or $A_3$ are replaced by an fluorine atom(s).

(25) The liquid crystalline alkenyltolan derivative recited in paragraph (4) above wherein G represents a covalent bond, t+m=4, and a double bond exists at a terminal of the molecule.

(26) The liquid crystalline alkenyltolan derivative recited in paragraph (4) above wherein G represents a covalent bond, t+m=5, and a double bond exists at a second position counting from a terminal of the molecule.

(27) The liquid crystalline alkenyltolan derivative recited in paragraph (1) above wherein $B_1$, $B_2$, and $B_3$ independently represent a covalent bond, an 1,2-ethylene, 1,2-ethynylene, oxymethylene, methylenoxy, carbonyloxy, or 1,4-butylene group.

(28) A liquid crystal composition comprising at least two components and comprising at least one liquid crystalline compound recited in any one of paragraphs (1) to (27) above.

(29) A liquid crystal composition comprising, as a first component, at least one liquid crystalline compound recited in any one of paragraphs (1) to (27) above, and comprising, as a second component, at least one compound selected from the group consisting of the compounds expressed by any one of the general formulas (2), (3), and (4)

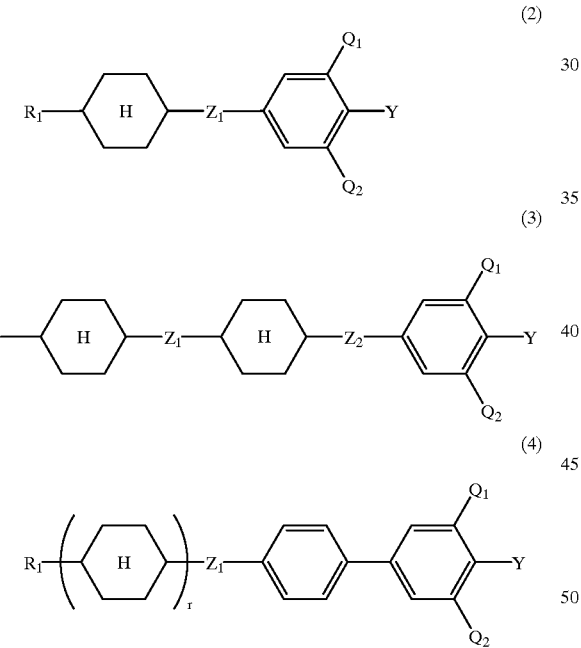

wherein $R_1$ represents an alkyl group or alkyloxy group having 1 to 10 carbon atoms; Y represents a fluorine atom or a chlorine atom; $Q_1$ and $Q_2$ independently represent a hydrogen atom or a fluorine atom; r is 1 or 2; and $Z_1$ and $Z_2$ independently represent a covalent bond or —$CH_2CH_2$—.

(30) A liquid crystal composition comprising, as a first component, at least one compound recited in any one of paragraphs (1) to (27) above, and comprising, as a second component, at least one compound selected from the group consisting of the compounds expressed by any one of the general formulas (5), (6), (7), (8), and (9)

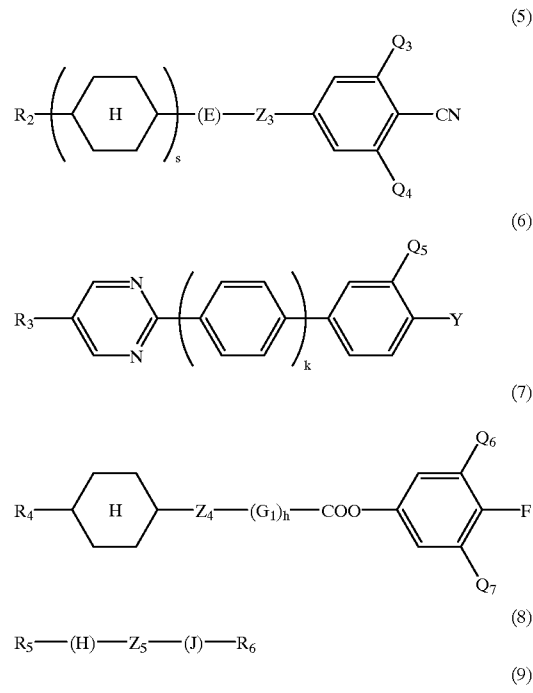

wherein $R_2$ represents an alkyl group having 1 to 10 carbon atoms or an alkenyl group having 2 to 10 carbon atoms, and any methylene group (—$CH_2$—) in the alkyl or the alkenyl group may be replaced by an oxygen atom (—O—), but adjacent two or more methylene groups are not replaced by an oxygen atom(s) simultaneously; $Z_3$ represents a covalent bond, —$CH_2CH_2$—, or —COO—; $Q_3$ and $Q_4$ independently represent a hydrogen atom or a fluorine atom; (E) represents an 1,4-cyclohexylene, 1,4-phenylene, or dioxane-2,5-diyl group; s is 0 or 1; $R_3$ represents an alkyl group having 1 to 10 carbon atoms; $Q_5$ represents a hydrogen atom or a fluorine atom; k is 0 or 1; $R_4$ represents an alkyl group having 1 to 10 carbon atoms; ($G_1$) represents an 1,4-cyclohexylene or 1,4-phenylene group; $Q_6$ and $Q_7$ independently represent a hydrogen atom or a fluorine atom; $Z_4$ represents a covalent bond or —COO—; h is 0 or 1; $R_5$ and $R_6$ independently represent an alkyl group, alkyloxy group, or alkyloxymethyl group, each having 1 to 10 carbon atoms; (H) represents an 1,4-cyclohexylene, pyrimidine-2,5-diyl, or 1,4-phenylene group; (J) represents an 1,4-cyclohexylene or 1,4-phenylene group; $Z_5$ represents a covalent bond, —$CH_2CH_2$—, —C≡C—, or —COO—; $R_7$ represents an alkyl group or alkyloxy group, each having 1 to 10 carbon atoms; $R_8$ represents an alkyl group, alkyloxy group, or alkyloxymethyl group, each having 1 to 10 carbon atoms; (K) represents an 1,4-cyclohexylene or pyrimidine-2,5-diyl group; (L) and (M) independently represent an 1,4-cyclohexylene or 1,4-phenylene group; $Z_6$ represents a covalent bond, —$CH_2CH_2$—, or —COO—; $Z_7$ represents a covalent bond, —C≡C—, or —COO—; and $Q_8$ represents a hydrogen atom or a fluorine atom.

(31) A liquid crystal display device including a liquid crystal composition comprising at least 2 components and comprising at least one liquid crystalline compound recited in any one of paragraphs (1) to (27) above.

(32) A liquid crystal display device including a liquid crystal composition recited in any one of paragraphs (28) to (30) above.

BEST MODE FOR CARRYING OUT THE INVENTION

Among the liquid crystalline compounds of the present invention expressed by the general formula (1), a group of compounds expressed by the general formulas (1-a) to (1-s) are preferable.

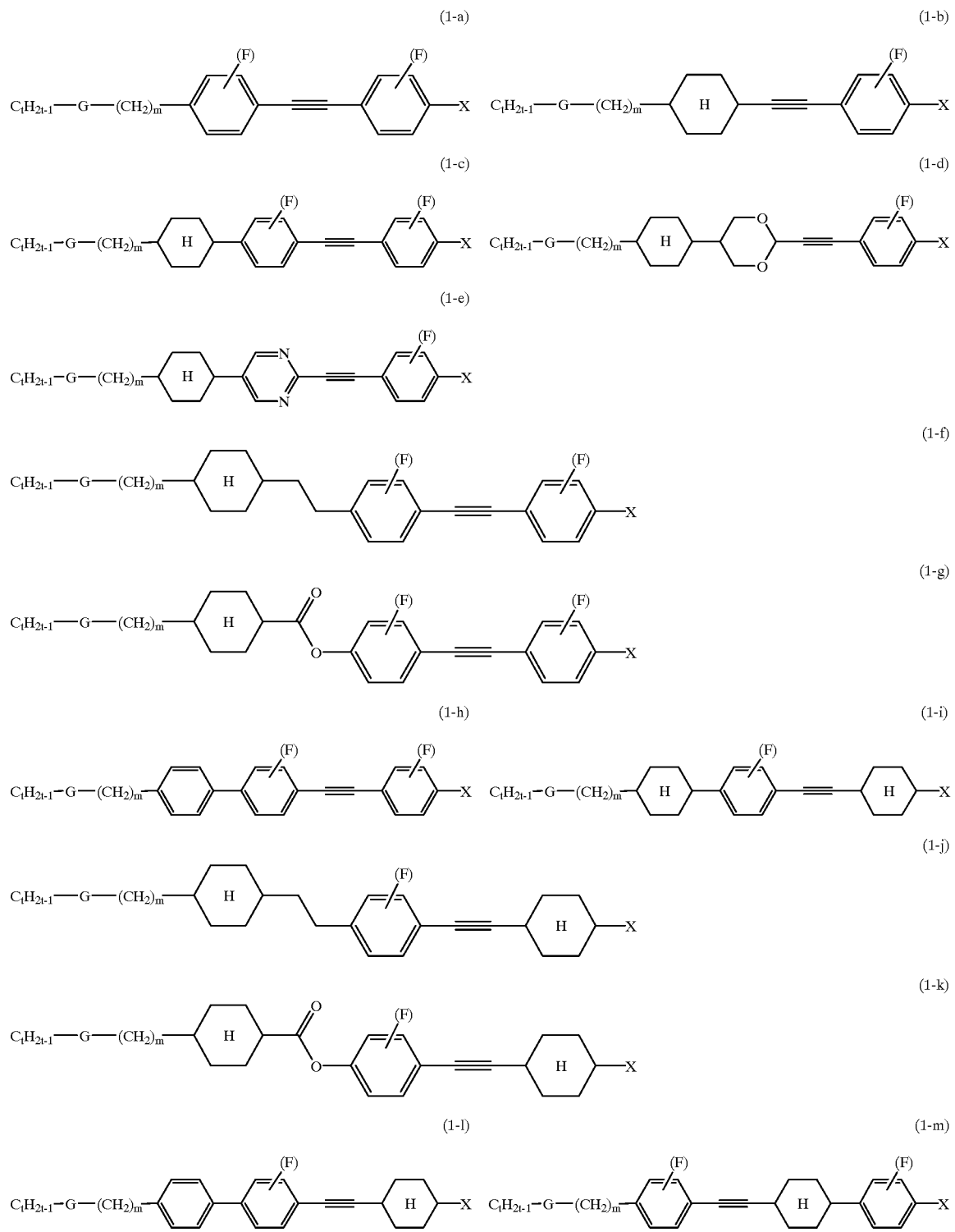

-continued

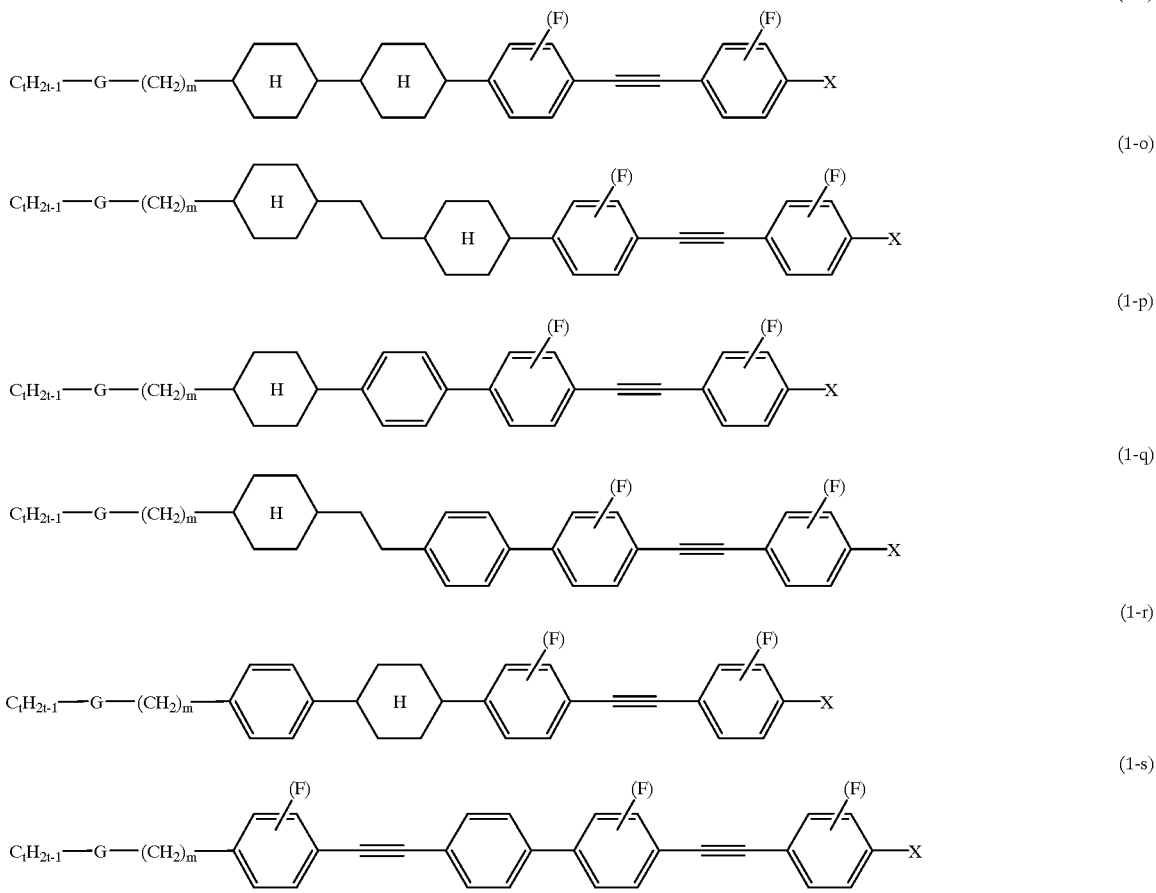

(1-n)
(1-o)
(1-p)
(1-q)
(1-r)
(1-s)

wherein G, t, m, and X have the same meaning as described above.

Any of these compounds of the present invention is characterized by having high Δn. Also, these compounds are excellent in miscibility with other liquid crystal compounds, are low in viscosity, and are highly stable chemically and physically.

Any of liquid crystalline compounds of the present invention exhibits preferable physical properties. Particularly, compounds expressed by the formulas (1-n) to (1-s) can be used for liquid crystal compositions having high upper limit temperature of liquid crystal phase since they have high clearing point, and compounds expressed by the formula (1-a) and (1-b) can be used for liquid crystal compositions having low upper limit temperature of liquid crystal phase.

When liquid crystal compositions having particularly large positive value of dielectric anisotropy are produced to lower driving voltage of display devices, liquid crystalline compounds having such characteristics (P type compounds) are used. Such purpose can be achieved by introducing a halogen atom or cyano group to X in the general formula (1), or by introducing 1,4-phenylene ring in which a hydrogen atom(s) is replaced by a fluorine atom(s) to $A_1$, $A_2$, $A_3$, and/or $A_4$. Especially, compounds expressed by the formula (1-d), (1-e), (1-g), or (1-k) are P type compounds having particularly remarkable characteristics, and are useful for such purpose.

Compounds having negative or small positive dielectric anisotropy (N type compounds) are obtained by introducing an alkyl group having small dipole moment to X in the general formula (1). Particularly, compounds having negative dielectric anisotropy can be obtained by introducing 1,4-phenylene in which a hydrogen atom(s) at 2 and/or 3 position is replaced by a fluorine atom(s), to $A_1$, $A_2$, $A_3$ and/or $A_4$.

Any compounds expressed by the general formula (1) have high Δn, and the compounds expressed by the formula (1-h), (1-p), (1-q), (1-r), or (1-s) are very useful since they have extremely high Δn.

Not of all liquid crystalline compounds of the present invention expressed by the general formula (1) are necessarily exhibit liquid crystal phase. However, any liquid crystalline compounds expressed by the general formula (1) have good miscibility with other liquid crystal compounds and do not lower or reduce the temperature range of nematic phase of the other liquid crystalline compounds when mixed therewith. Accordingly, the liquid crystalline compounds expressed by the general formula (1) and having excellent optical characteristics as described above become useful components for liquid crystal compositions even when the compounds themselves do not exhibit liquid crystal phase. Besides, each of the elements in the compounds may be an isotope since the characteristics of liquid crystalline compounds expressed by the general formula (1) are not affected even when the element is replaced by the isotope.

The liquid crystal compositions of the present invention comprise at least one liquid crystalline compound expressed by the general formula (1) in the range of 0.1 to 99.9% by weight, and the compositions preferably comprise a first component comprising at least one compound expressed by the general formula (1), and a compound selected from the group consisting of the compounds expressed by any one of the general formulas (2) to (9) depending on the physical properties of liquid crystal compositions to be obtained.

As compounds which are preferably used for the liquid crystal compositions of the present invention and are expressed by any one of the general formulas (2) to (4), the following compounds (2-1) to (4-41) can be mentioned as examples:

(2-1)
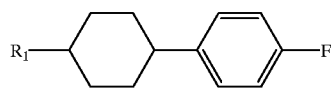

(2-2)
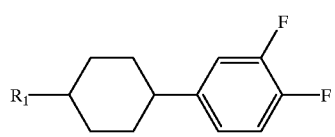

(2-3)
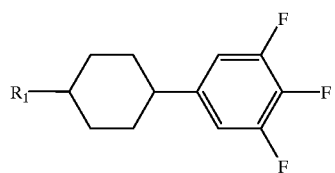

(2-4)
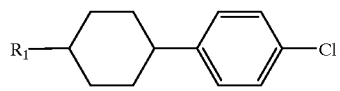

(2-5)
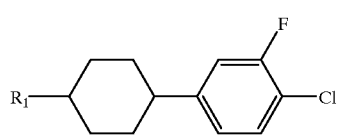

(2-6)
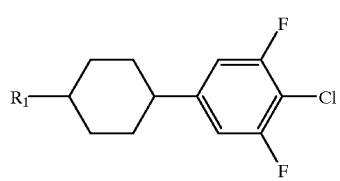

(2-7)
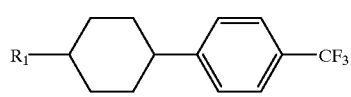

(2-8)
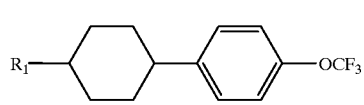

(2-9)
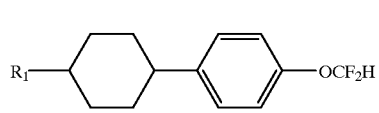

-continued (2-10)
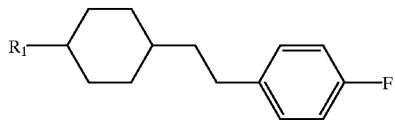

(2-11)
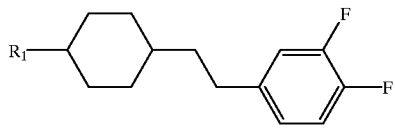

(2-12)
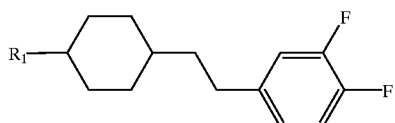

(2-13)
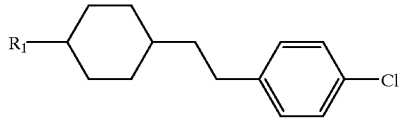

(2-14)
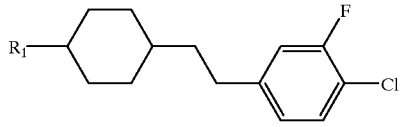

(2-15)
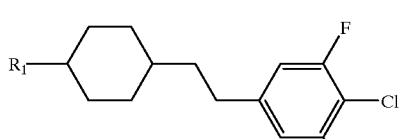

(3-1)
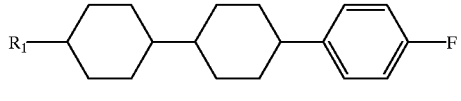

(3-2)
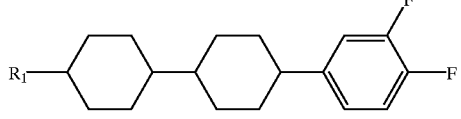

(3-3)
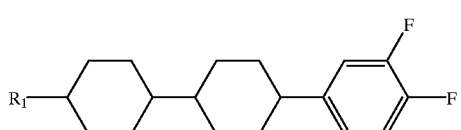

(3-4)
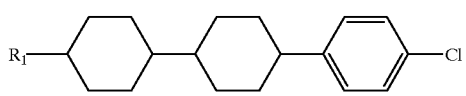

(3-5), (3-6), (3-7), (3-8), (3-9), (3-10), (3-11), (3-12), (3-13), (3-14), (3-15), (3-16), (3-17), (3-18), (3-19), (3-20), (3-21)

(3-22)
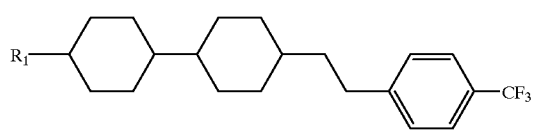
(3-23)
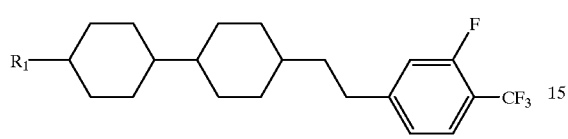
(3-24)
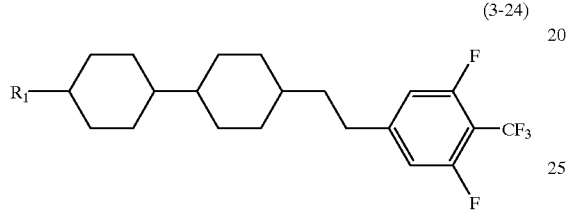
(3-25)
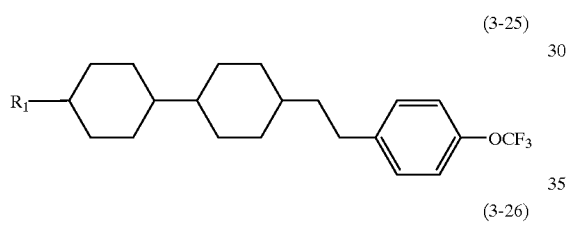
(3-26)
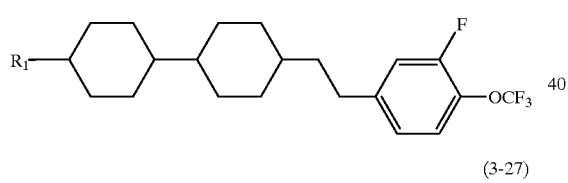
(3-27)
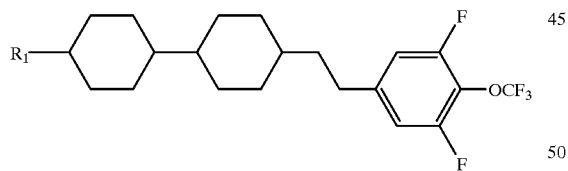
(3-28)
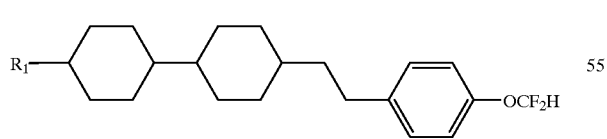
(3-29)
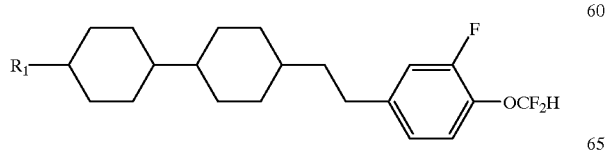
(3-30)
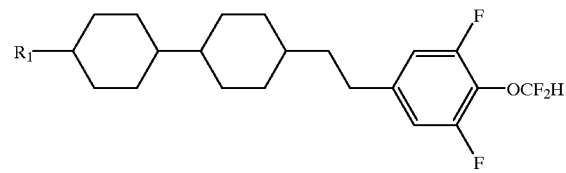
(3-31)
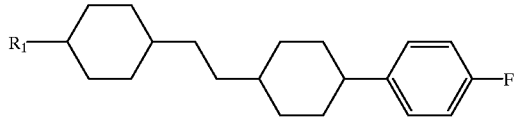
(3-32)
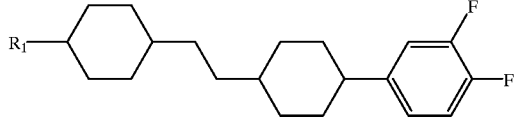
(3-33)
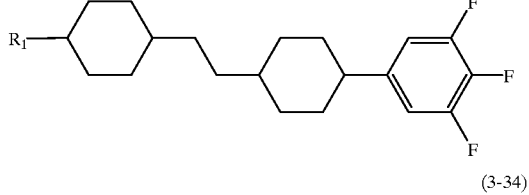
(3-34)
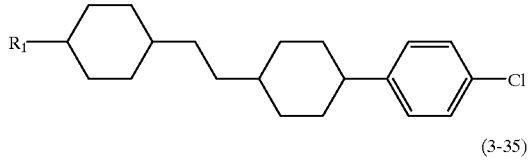
(3-35)
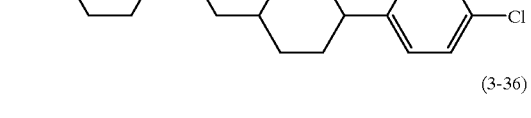
(3-36)
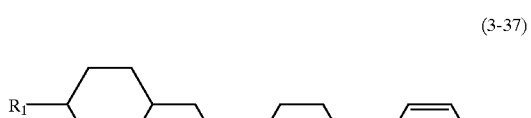
(3-37)
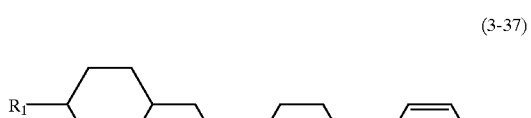

(3-38)
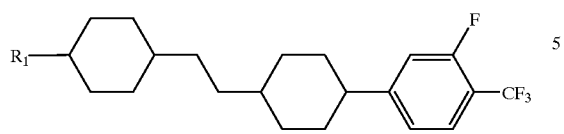
(3-39)
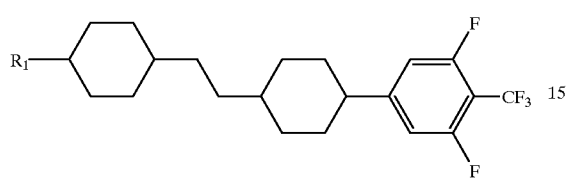
(3-40)
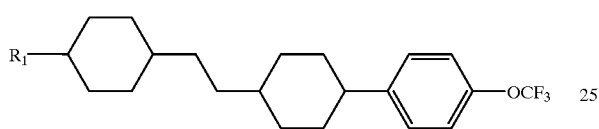
(3-41)
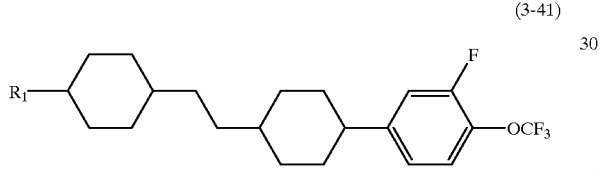
(3-42)
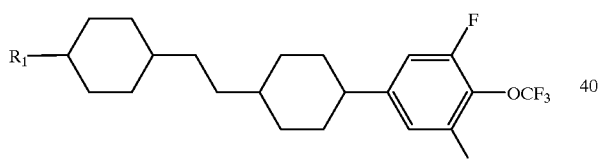
(3-43)
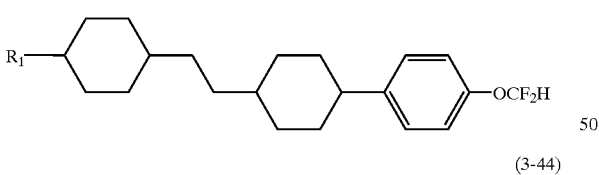
(3-44)
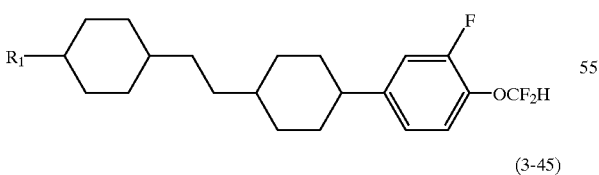
(3-45)
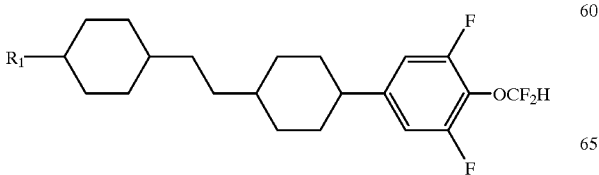
(3-46)
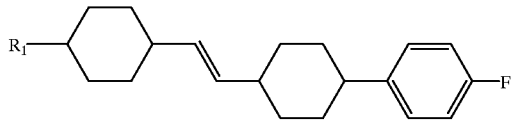
(3-47)
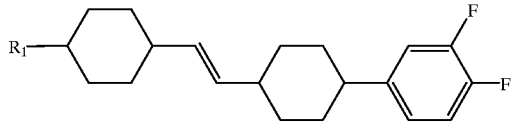
(3-48)
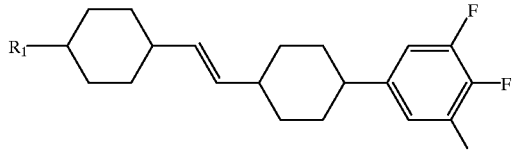
(4-1)
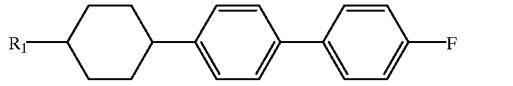
(4-2)
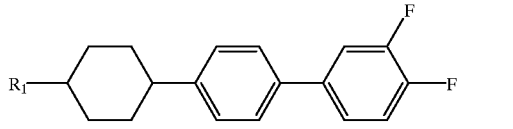
(4-3)
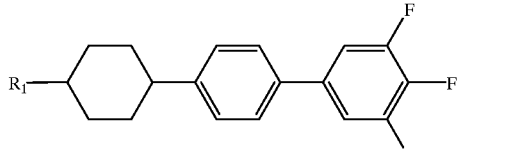
(4-4)
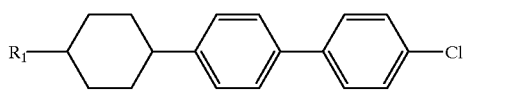
(4-5)
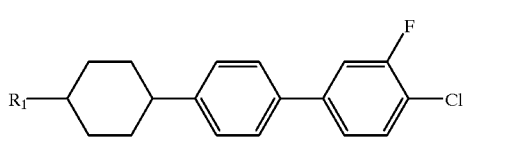
(4-6)
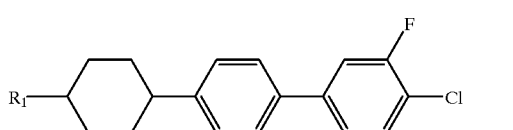

(4-7)
(4-8)
(4-9)
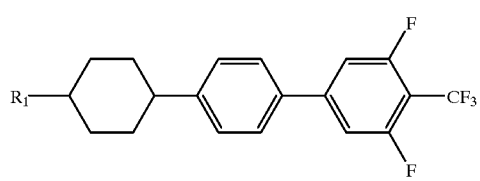
(4-10)
(4-11)
(4-12)
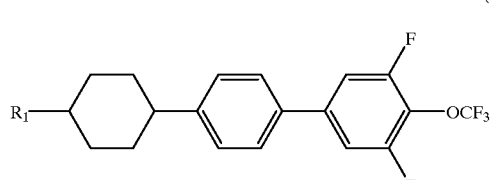
(4-13)
(4-14)
(4-15)
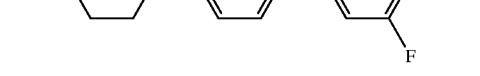
(4-16)
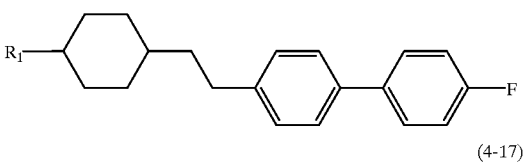
(4-17)
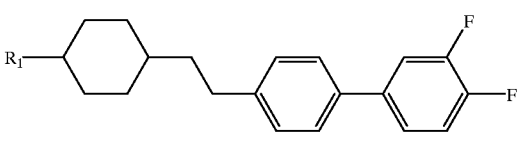
(4-18)
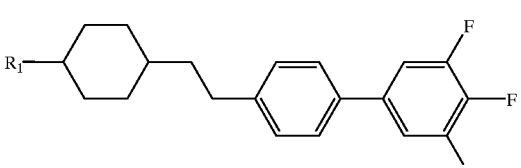
(4-19)
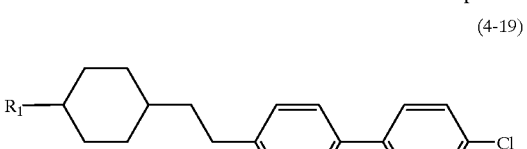
(4-20)
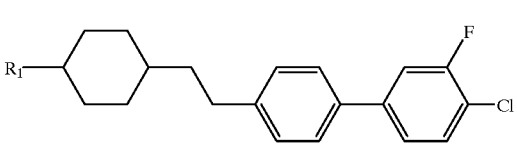
(4-21)
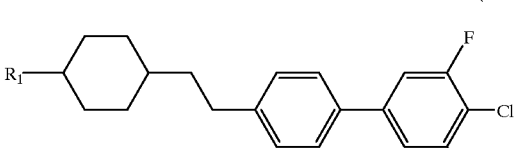
(4-22)
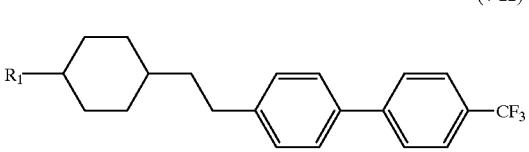
(4-23)
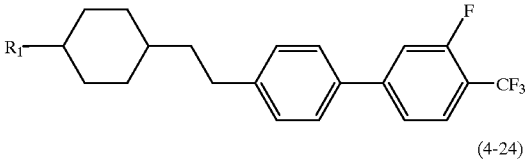
(4-24)
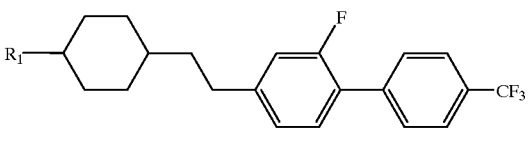

-continued
(4-25)
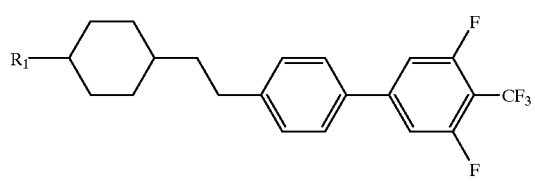
(4-26)
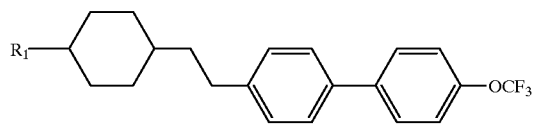
(4-27)
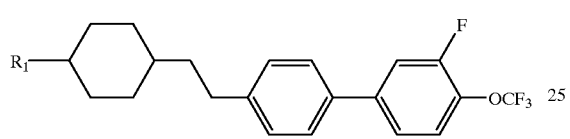
(4-28)
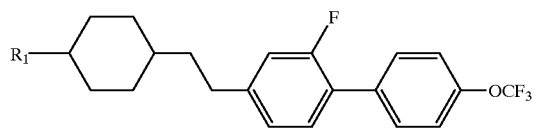
(4-29)
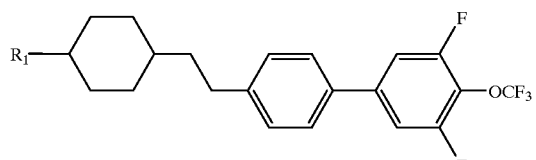
(4-30)
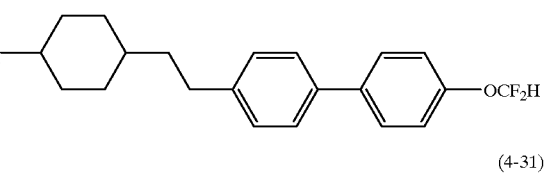
(4-31)
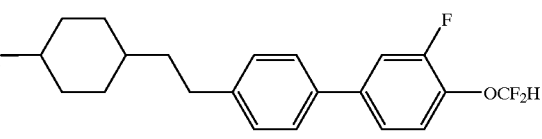
(4-32)
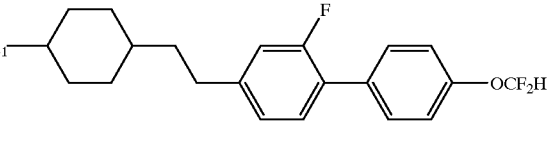
-continued
(4-33)
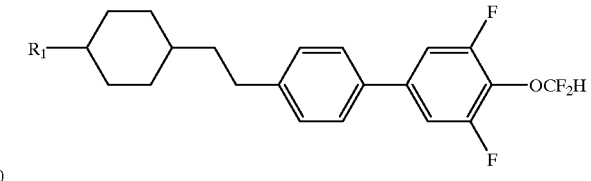
(4-34)
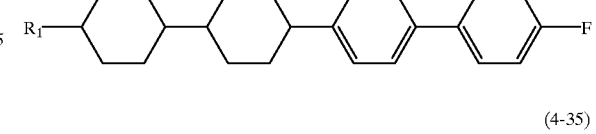
(4-35)
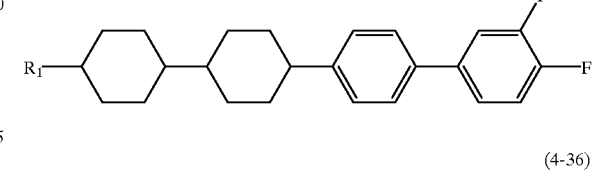
(4-36)
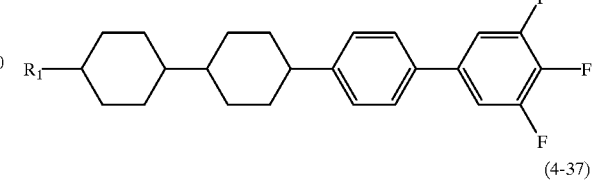
(4-37)
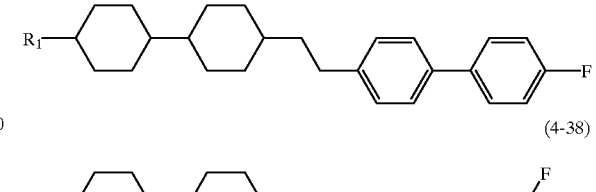
(4-38)
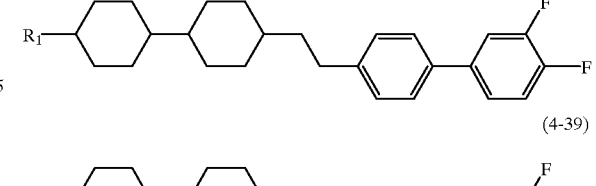
(4-39)
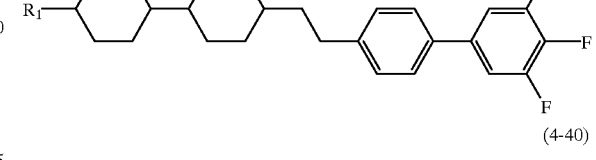
(4-40)
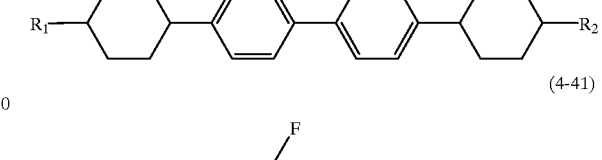
(4-41)
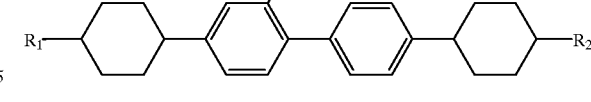

wherein $R_1$ represents an alkyl group or alkyloxy group having 1 to 10 carbon atoms.

Any compound expressed by any one of the general formulas (2) to (4) has positive dielectric anisotropy and are remarkably excellent in heat stability and chemical stability. When liquid crystal compositions for TFT (AM-LCD) are produced, the compounds are particularly useful since high reliability such as high voltage holding ratio and large resistivity are required for such compositions. Also, when liquid crystal compositions for STN display mode or ordinary TN display mode are produced, compounds expressed by one of the general formulas (2) to (4) can be used.

In the liquid crystal compositions of the present invention, the compounds expressed by any one of the general formulas (2) to (4) are used in an amount in the range of 1 to 99% by weight, preferably 10 to 97% by weight, and more desirably 40 to 95% by weight based on the total amount of liquid crystal composition when liquid crystal compositions for TFT are produced.

Liquid crystal compositions of the present invention may further comprise compounds expressed by any one of the general formulas (5) to (9).

As compounds which are preferably used for the liquid crystal compositions of the present invention and are expressed by any one of the general formulas (5) to (7), the following compounds (5-1) to (7-13) can be mentioned as examples:

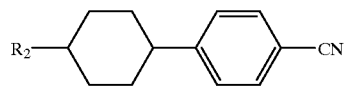 (5-1)

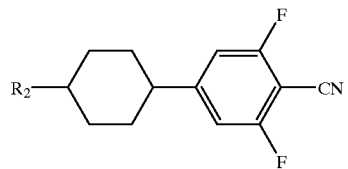 (5-2)

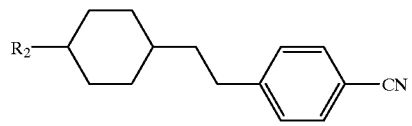 (5-3)

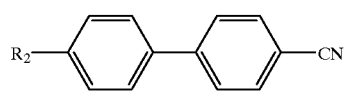 (5-4)

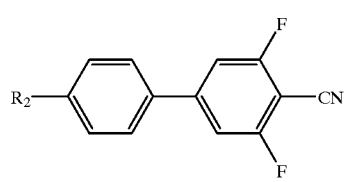 (5-5)

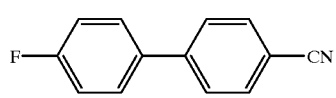 (5-6)

 (5-7)

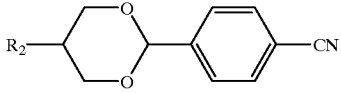 (5-8)

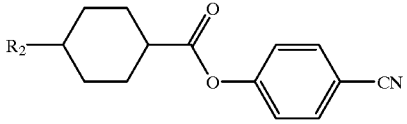 (5-9)

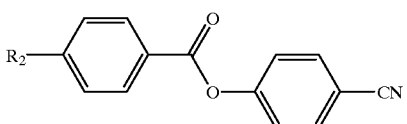 (5-10)

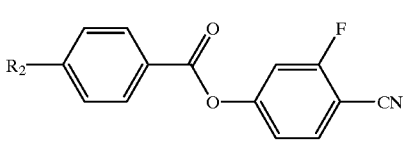 (5-11)

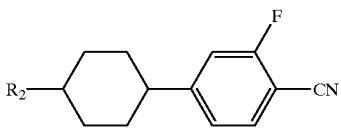 (5-12)

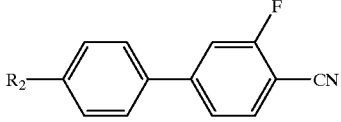 (5-13)

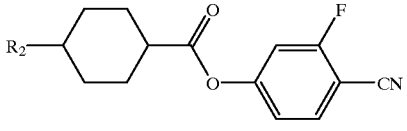 (5-14)

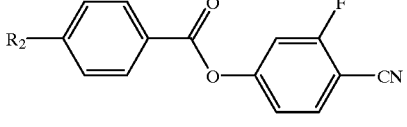 (5-15)

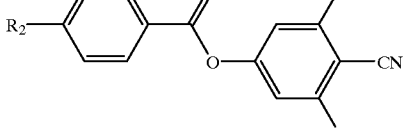 (5-16)

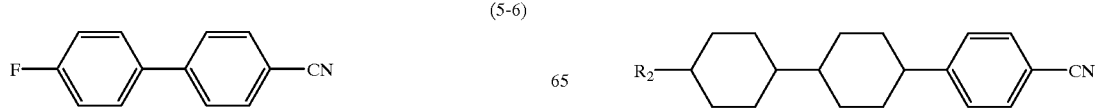 (5-17)

-continued
(5-18)
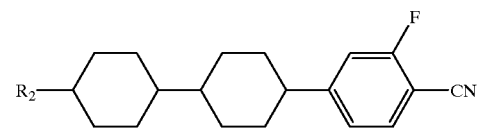
(5-19)
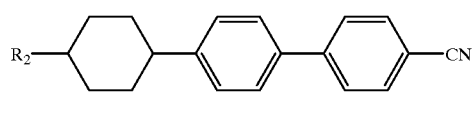
(5-20)
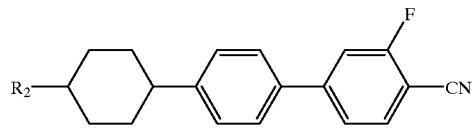
(5-21)
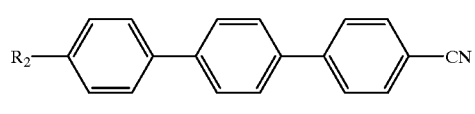
(5-22)
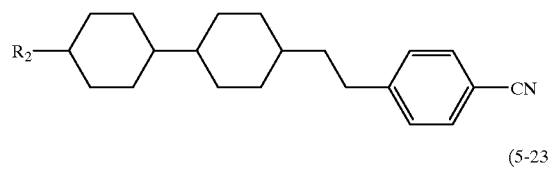
(5-23)
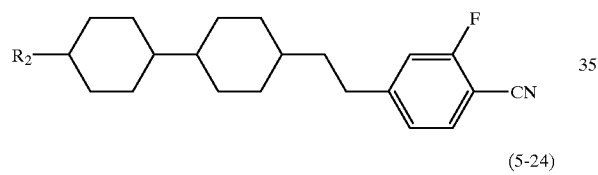
(5-24)
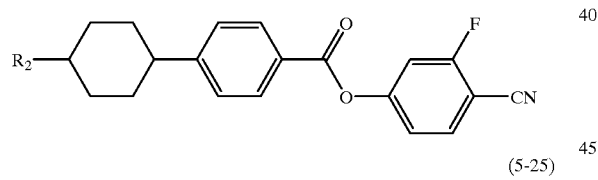
(5-25)
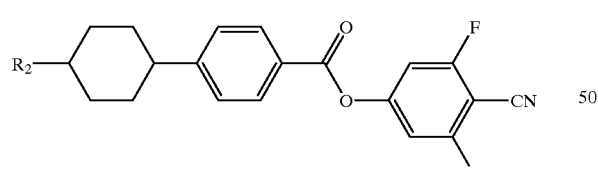
(5-26)
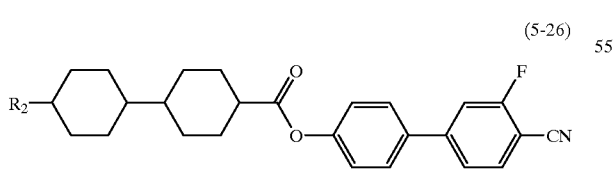
(5-27)
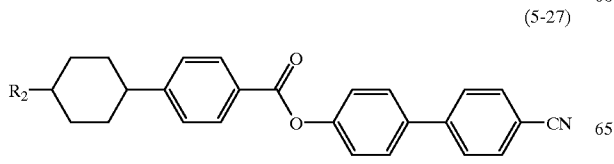
-continued
(6-1)
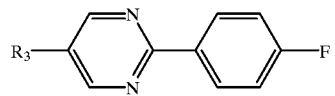
(6-2)
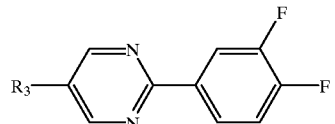
(6-3)
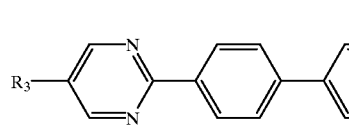
(7-1)
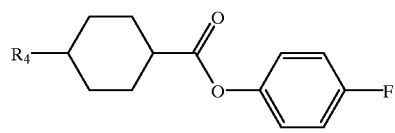
(7-2)
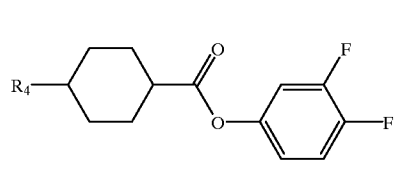
(7-3)
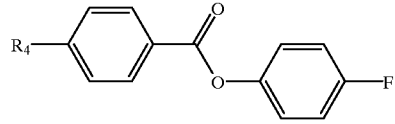
(7-4)
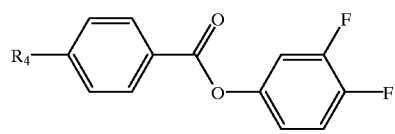
(7-5)
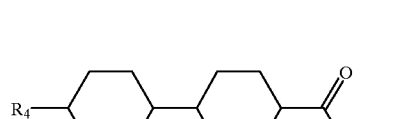
(7-6)
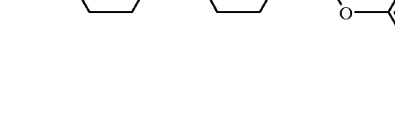
(7-7)
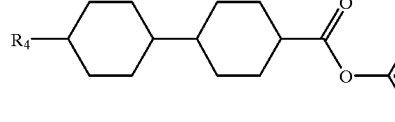

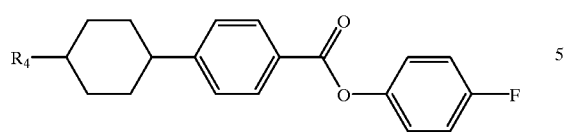 (7-8)

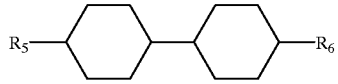 (8-1)

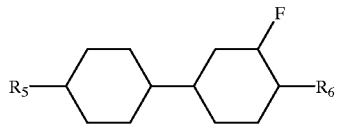 (8-2)

(7-9)
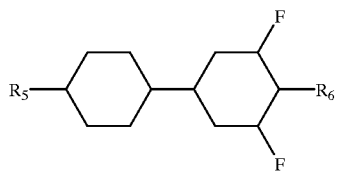 (8-3)

(7-10)
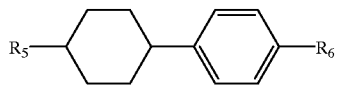 (8-4)

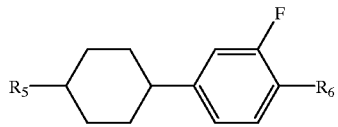 (8-5)

(7-11)
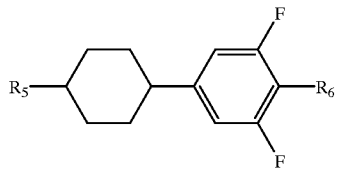 (8-6)

(7-12)
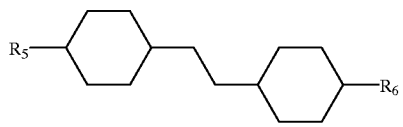 (8-7)

(7-13)
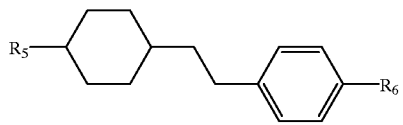 (8-8)

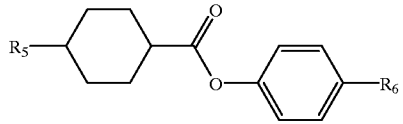 (8-9)

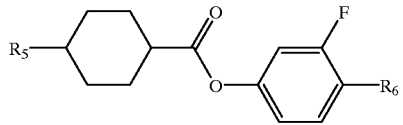 (8-10)

wherein $R_2$ represents an alkyl group having 1 to 10 carbon atoms or an alkenyl group having 2 to 10 carbon atoms, and any methylene group in the alkyl or alkenyl group may be replaced by an oxygen atom(s), but two or more methylene groups are not continuously replaced by oxygen atom(s); and $R_3$ and $R_4$ independently represent an alkyl group having 1 to 10 carbon atoms.

Since any compound expressed by any one of the general formulas (5) to (7) has positive and large value of dielectric anisotropy, the compound are used particularly for the purpose of lowering threshold voltage of liquid crystal compositions. The compounds are used also for the purpose of widening nematic range such as raising clearing point, and for the purpose of adjusting viscosity, adjusting optical anisotropy, or improving the steepness of threshold characteristics.

As the compounds which are preferably used for the liquid crystal compositions of the present invention and expressed by the general formula (8) or (9), the following compounds (8-1) to (9-14) can be mentioned as examples:

-continued

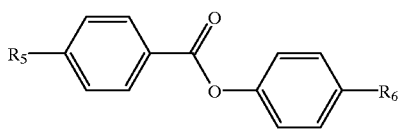 (8-11)

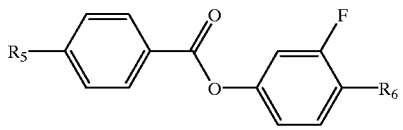 (8-12)

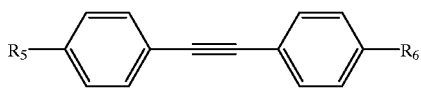 (8-13)

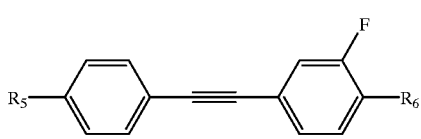 (8-14)

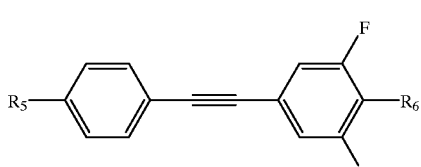 (8-15)

 (9-1)

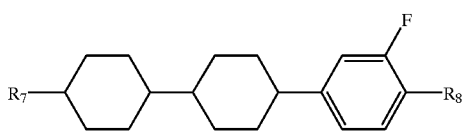 (9-2)

 (9-3)

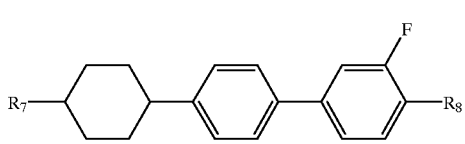 (9-4)

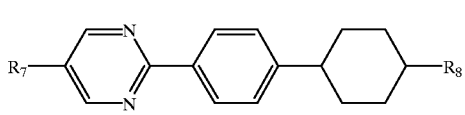 (9-5)

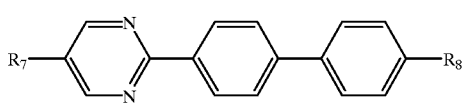 (9-6)

-continued

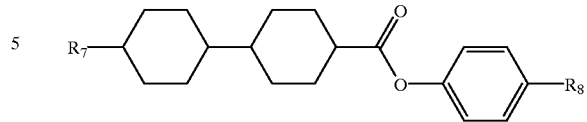 (9-7)

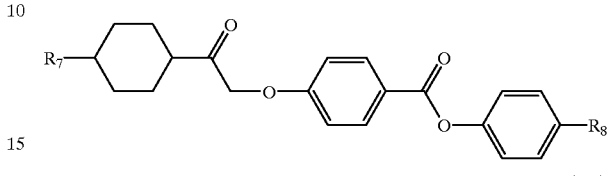 (9-8)

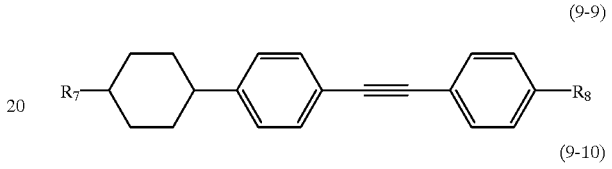 (9-9)

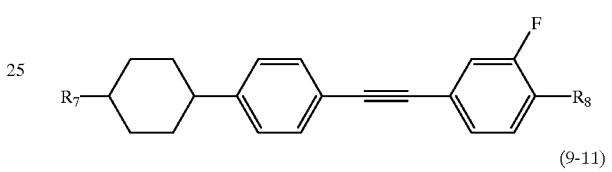 (9-10)

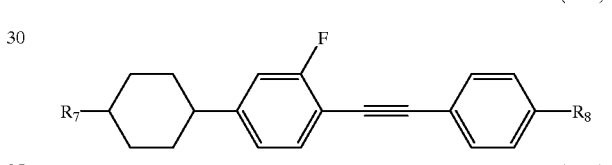 (9-11)

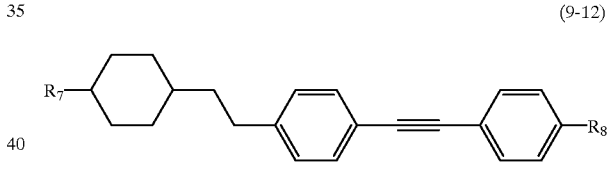 (9-12)

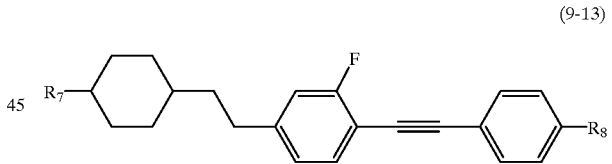 (9-13)

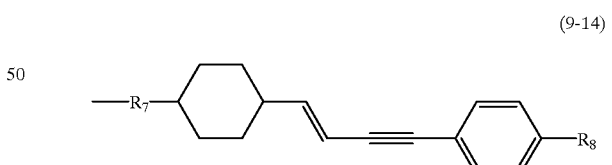 (9-13)

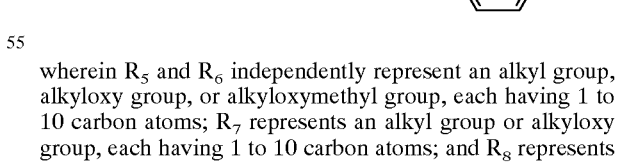 (9-14)

wherein $R_5$ and $R_6$ independently represent an alkyl group, alkyloxy group, or alkyloxymethyl group, each having 1 to 10 carbon atoms; $R_7$ represents an alkyl group or alkyloxy group, each having 1 to 10 carbon atoms; and $R_8$ represents an alkyl group, alkyloxy group, or alkyloxymethyl group, each having 1 to 10 carbon atoms.

Any compound expressed by the general formula (8) or (9) has negative, or small and positive dielectric anisotropy. The compounds expressed by the general formula (9) are used for the purpose of widening nematic range such as raising clearing point of liquid crystal compositions and/or for the purpose of adjusting optical anisotropy.

As described above, any compound expressed by any one of the general formulas (5) to (9) is useful in the production of liquid crystal compositions for ordinary TN display mode, and particularly for STN display mode.

In the liquid crystal compositions of the present invention, the compounds expressed by any one of the general formulas (5) to (9) are used in an amount in the range of 1- to 99% by weight, preferably 10 to 97% by weight, and more desirably 40 to 95% by weight based on the total amount of liquid crystal composition when liquid crystal compositions for TN display mode or STN display mode are produced. Further, compounds expressed by any one of the general formulas (2) to (4) may be used together.

By using the liquid crystal compositions of the present invention for TFT liquid crystal display devices, the steepness of threshold characteristic, or viewing angle can be improved. The response speed of liquid crystal compositions comprising the compounds are improved, since the compounds expressed by the general formula (1) have low viscosity.

Liquid crystal compositions of the present invention can be produced by conventional methods, for example, a method wherein various components are dissolved each other at high temperature. Further, the liquid crystal compositions of the present invention can be improved or optimized as intended according to their uses by adding a suitable substance. Such additive is well known in the art and described in detail in the literature. For instance, a chiral dopant or the like can be added to induce a helical structure of liquid crystals thereby adjust the required twisting angle, and to avoid the reverse-twist.

Further, a dichroic dye such as merocyanine type, styryl type, azo type, azomethine type, azoxy type, quinophthalone type, anthraquinone type, or tetrazine type dye can be added to the liquid crystal compositions of the present invention in the purpose of using the compositions as ones for guest-host (GH) mode. The liquid crystal compositions of the present invention can be used as NCAP prepared by the microencapsulation of a nematic liquid crystal, or as liquid crystal compositions for polymer dispersed liquid crystal display devices (PDLCD) represented by polymer network liquid crystal display devices (PNLCD) prepared by forming polymers of three-dimensional reticulated structure in a liquid crystal. Further, the liquid crystal compositions of the present invention can be used as ones for electrically controlled birefringence (ECB) mode or dynamic scattering (DS) mode.

As nematic liquid crystal compositions comprising the liquid crystalline compounds of the present invention and produced by the methods described above, the following examples of composition can be mentioned:

Abbreviation used when the composition examples are indicated are defined in the following Table 1.

TABLE 1

| Left side terminal group | Symbol | Bonding group | Symbol |
|---|---|---|---|
| $C_aH_{2a+1}$— | a- | —$CH_2CH_2$— | 2 |
| $C_aH_{2a+1}O$— | aO- | —COO— | E |
| CaH2a + 10cbH2b— | aOb- | —C≡C— | T |
| CH=$CHC_aH_{2a}$— | Va- | —CH=CH— | V |
| $C_aH_{2a+1}CH=CHC_bH_{2b}$— | aVb- | —$CF_2O$— | CF2O |
| $C_aH_{2a+1}CH=CHC_bH_{2b}CH=CHC_dH_{2d}$— | aVbVd- | —$OCF_2$— | OCF2 |
| $CH_2=CHC_aH_{2a}O$— | VaO- | | |

| Ring structure | Symbol | Right side terminal group | Symbol |
|---|---|---|---|
|  | B | —F | —F |
| 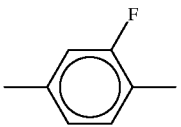 | B(F) | —Cl | —CL |
| 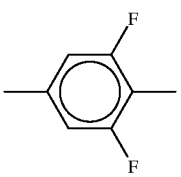 | B(F,F) | —CN | —C |
|  | H | —$CF_3$ | —CF3 |

TABLE 1-continued

| | | | |
|---|---|---|---|
|  | Py | —OCF$_3$ | —OCF3 |
|  | D | —OCF$_2$H | —OCF2H |
| 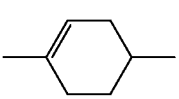 | Ch | —C$_w$H$_{2w+1}$ | —w |
| | | —OC$_w$H$_{2w+1}$ | -Ow |
| | | —COOCH$_3$ | -EMe |

COMPOSITION EXAMPLE 1

| | |
|---|---|
| V2-HBTB-2 | 10.0% |
| V2-HB(F,F)TB-2 | 8.0% |
| V2-HB-C | 12.0% |
| 1V2-HB-C | 11.0% |
| 1V2-BEB(F,F)-C | 11.0% |
| 2-BTB-1 | 8.0% |
| 4-BTB-O2 | 8.0% |
| 5-BTB-O1 | 6.0% |
| 3-HH-4 | 3.0% |
| 3-HH-EMe | 3.0% |
| 3-H2BTB-2 | 4.0% |
| 3-H2BTB-3 | 4.0% |
| 3-H2BTB-4 | 4.0% |
| 2-H2BTB-3 | 4.0% |
| 2-H2BTB-2 | 4.0% |

COMPOSITION EXAMPLE 2

| | |
|---|---|
| V2-HBTB-2 | 10.0% |
| 3-HB-C | 30.0% |
| 5-HB-C | 10.0% |
| 2-BTB-1 | 10.0% |
| 3-HH-4 | 10.0% |
| 3-HHB-1 | 10.0% |
| 3-HHB-3 | 11.0% |
| 3-H2BTB-2 | 3.0% |
| 3-H2BTB-3 | 3.0% |
| 3-H2BTB-4 | 3.0% |

COMPOSITION EXAMPLE 3

| | |
|---|---|
| V2-HBTB-2 | 6.0% |
| V2-BTB-1 | 9.0% |
| 3O1-BEB(F)-C | 11.0% |
| V2-HB-C | 11.0% |
| 3-HB-O2 | 3.0% |
| 2-BTB-O1 | 5.0% |
| 3-BTB-O1 | 5.0% |
| 4-BTB-O1 | 5.0% |
| 4-BTB-O2 | 5.0% |
| 5-BTB-O1 | 5.0% |
| 3-HHB-O1 | 3.0% |
| 3-H2BTB-2 | 2.0% |

-continued

| | |
|---|---|
| 3-H2BTB-3 | 3.0% |
| 3-H2BTB-4 | 3.0% |
| 3-HB(F)TB-2 | 4.0% |
| 3-HB(F)TB-3 | 4.0% |
| 3-HB(F)TB-4 | 4.0% |
| 2-PyBH-3 | 4.0% |
| 3-PyBH-3 | 4.0% |
| 3-PyBH-2 | 4.0% |

COMPOSITION EXAMPLE 4

| | |
|---|---|
| V2-BTB-1 | 5.0% |
| 2-HB(F)-C | 14.0% |
| 3-HB(F)-C | 13.0% |
| 5-HB(F)-C | 9.0% |
| 2-BB-C | 8.0% |
| 2-BEB-C | 12.0% |
| 3-BEB-C | 4.0% |
| 2-HHB(F)-C | 9.0% |
| 3-HHB(F)-C | 12.0% |
| 2-HHB-C | 3.0% |
| 3-HHB-C | 3.0% |
| 3-PyBB-F | 6.0% |
| 5-PyB-F | 2.0% |

COMPOSITION EXAMPLE 5

| | |
|---|---|
| V2-HBTB-1 | 6.0% |
| 3-DB-C | 10.0% |
| 4-DB-C | 10.0% |
| 2-BEB-C | 12.0% |
| 3-BEB-C | 4.0% |
| 3-HHEBB-C | 3.0% |
| 5-HHEBB-C | 3.0% |
| 5-HEB-F | 3.0% |
| 3-PyB(F)-F | 6.0% |
| 3-HEB-O4 | 8.9% |
| 4-HEB-O2 | 5.9% |
| 5-HEB-O1 | 5.9% |
| 3-HEB-O2 | 5.4% |
| 5-HEB-O2 | 5.9% |

-continued

| | |
|---|---|
| 1O-BEB-2 | 3.0% |
| 5-HEB-1 | 3.0% |
| 4-HEB-4 | 5.0% |

COMPOSITION EXAMPLE 6

| | |
|---|---|
| V1O-HBTB-1 | 4.0% |
| V2-DBTB-CL | 3.0% |
| 3-HHEB-F | 2.0% |
| 3-HBEB-F | 2.0% |
| 3-HHB-F | 4.0% |
| 3-HB-O2 | 14.0% |
| 3-HB-O4 | 13.0% |
| 3-PyB-4 | 3.1% |
| 4-PyB-4 | 3.1% |
| 6-PyB-4 | 3.2% |
| 3-PyB-5 | 3.2% |
| 4-PyB-5 | 3.2% |
| 6-PyB-5 | 3.2% |
| 6-PyB-O5 | 6.0% |
| 6-PyB-O6 | 6.0% |
| 6-PyB-O7 | 6.0% |
| 6-PyB-O8 | 6.0% |
| 2-HHB-1 | 4.0% |
| 3-HHB-3 | 6.0% |
| 3-HHB-O1 | 5.0% |

COMPOSITION EXAMPLE 7

| | |
|---|---|
| V2-BTB-1 | 5.0% |
| V2-HB(F,F)TB-2 | 4.0% |
| V2-HB-C | 9.0% |
| 1V2-HB-C | 9.0% |
| 3-HB-C | 14.0% |
| 1O1-HB-C | 8.0% |
| 2O1-HB-C | 4.0% |
| 2-HHB-C | 3.0% |
| 3-HHB-C | 5.0% |
| 3-HH-4 | 10.0% |
| 1O1-HH-5 | 8.0% |
| 2-BTB-O1 | 11.0% |
| 3-HHB-1 | 6.0% |
| 3-HEBEB-1 | 2.0% |
| 3-HEBEB-F | 2.0% |

COMPOSITION EXAMPLE 8

| | |
|---|---|
| V2-HB(F,F)TB-2 | 10.0% |
| 3-H2HB(F,F)-F | 8.0% |
| 5-H2HB(F,F)-F | 8.0% |
| 3-HHB(F,F)-F | 8.0% |
| 4-HHB(F,F)-F | 6.0% |
| 3-HH2B(F,F)-F | 10.0% |
| 5-HH2B(F,F)-F | 8.0% |
| 3-HBB(F,F)-F | 14.0% |
| 5-HBB(F,F)-F | 10.0% |
| 3-HHEB(F,F)-F | 6.0% |
| 4-HHEB(F,F)-F | 3.0% |
| 3-HBEB(F,F)-F | 3.0% |
| 3-HHBB(F,F)-F | 3.0% |
| 3-HH2BB(F,F)-F | 3.0% |

COMPOSITION EXAMPLE 9

| | |
|---|---|
| V2-BTB-1 | 8.0% |
| V2-HBTB-2 | 5.0% |
| 7-HB(F)-F | 14.0% |
| 2-HHB(F)-F | 10.0% |
| 3-HHB(F)-F | 10.0% |
| 5-HHB(F)-F | 10.0% |
| 2-H2HB(F)-F | 6.0% |
| 3-H2HB(F)-F | 3.0% |
| 5-H2HB(F)-F | 6.0% |
| 2-HBB(F)-F | 7.0% |
| 3-HBB(F)-F | 7.0% |
| 5-HBB(F)-F | 14.0% |

COMPOSITION EXAMPLE 10

| | |
|---|---|
| V2-HBTB-CL | 6.0% |
| V2-HBTH-1 | 3.0% |
| 5-HB-CL | 7.0% |
| 7-HB(F,F)-F | 10.0% |
| 2-HBB(F)-F | 8.0% |
| 3-HBB(F)-F | 8.0% |
| 5-HBB(F)-F | 16.0% |
| 4-HHB-CL | 10.0% |
| 5-HHB-CL | 5.0% |
| 3-HBB(F,F)-F | 11.0% |
| 5-HBB(F,F)-F | 11.0% |
| 3-HB(F)VB-2 | 5.0% |

COMPOSITION EXAMPLE 11

| | |
|---|---|
| 1V2-HBTB-1 | 5.0% |
| 5-H2B(F)-F | 4.0% |
| 2-HHB(F)-F | 12.0% |
| 3-HHB(F)-F | 12.0% |
| 5-HHB (F)-F | 12.0% |
| 2-HBB(F)-F | 4.0% |
| 3-HBB(F)-F | 4.0% |
| 5-HBB(F)-F | 8.0% |
| 4-H2BB(F)-F | 4.0% |
| 3-HHB(F,F)-F | 7.0% |
| 5-HHB(F,F)-F | 4.0% |
| 3-HH2B(F,F)-F | 9.0% |
| 5-HH2B(F,F)-F | 6.0% |
| 5-H2BB(F,F)-F | 5.0% |
| 3-HBB-F | 2.0% |
| 5-HHEBB-F | 2.0% |

COMPOSITION EXAMPLE 12

| | |
|---|---|
| V2-HB(F,F)TB-2 | 5.0% |
| V2-HB(F,F)TB-3 | 5.0% |
| 7-HB(F,F)-F | 4.0% |
| 3-H2HB(F,F)-F | 12.0% |
| 4-H2HB(F,F)-F | 10.0% |
| 3-HHB(F,F)-F | 10.0% |
| 4-HHB(F,F)-F | 5.0% |
| 3-HH2B(F,F)-F | 15.0% |
| 5-H2B(F,F)-F | 10.0% |
| 3-HBB(F,F)-F | 12.0% |
| 5-HBB(F,F)-F | 10.0% |
| 1O1-HBBH-3 | 2.0% |

COMPOSITION EXAMPLE 13

| | |
|---|---|
| V2-HB(F,F)TB-2 | 6.0% |
| V2-BTB-1 | 4.0% |
| 6-HB-F | 8.0% |
| 7-HB-F | 8.0% |
| 5-HB-3 | 5.0% |
| 3-HB-O1 | 5.0% |
| 3-HHB-OCF3 | 6.0% |
| 4-HHB-OCF3 | 5.0% |
| 5-HHB-OCF3 | 5.0% |
| 3-HHEB-OCF3 | 2.0% |
| 3-HH2B-OCF3 | 3.0% |
| 5-HH2B-OCF3 | 3.0% |
| 3-HH2B-F | 3.0% |
| 5-HH2B-F | 3.0% |
| 3-HBB(F)-F | 6.0% |
| 5-HBB(F)-F | 5.0% |
| 3-HH2B(F)-F | 7.0% |
| 5-HH2B(F)-F | 9.0% |
| 3-HB(F,F)B(F)-F | 2.0% |
| 3-HB(F)BH-3 | 3.0% |
| 5-HB(F)BH-3 | 2.0% |

COMPOSITION EXAMPLE 14

| | |
|---|---|
| V2-HBTB-CL | 5.0% |
| V2-DBTB-CL | 5.0% |
| 5-HB-F | 7.0% |
| 3-HH-O1 | 7.0% |
| 3-HH-O3 | 6.0% |
| 3-HHB-OCHF2 | 3.0% |
| 5-HHB-OCHF2 | 4.0% |
| 3-HHB(F,F)-OCHF2 | 8.0% |
| 5-HHB(F,F)-OCHF2 | 8.0% |
| 2-HHB-OCF3 | 6.0% |
| 3-HHB-OCF3 | 7.0% |
| 4-HHB-OCF3 | 6.0% |
| 5-HHB-OCF3 | 6.0% |
| 3-HH2B(F)-F | 7.0% |
| 5-HH2B(F)-F | 9.0% |
| 3-HHEB(F)-F | 6.0% |

COMPOSITION EXAMPLE 15

| | |
|---|---|
| V2-HBTB-2 | 5.0% |
| V2-HBTB-1 | 5.0% |
| V-HB-C | 10.0% |
| 1V-HB-C | 5.0% |
| 5-BB-C | 5.0% |
| 2-HB(F)-C | 5.0% |
| 4-BB-3 | 3.0% |
| 3-H2B-O2 | 5.0% |
| 5-H2B-O2 | 5.0% |
| 3-BEB-C | 5.0% |
| 5-HEB-O1 | 8.0% |
| 5-HEB-O3 | 8.0% |
| 5-BBB-C | 5.0% |
| 4-BPyB-C | 4.0% |
| 4-BPyB-5 | 4.0% |
| 5-HB2B-4 | 5.0% |
| 5-HBB2B-3 | 3.0% |
| 1V-HH-1O1 | 5.0% |
| 1V2-HBB-3 | 5.0% |

COMPOSITION EXAMPLE 16

| | |
|---|---|
| V2-BTB-1 | 8.0% |
| V1O-HBTB-1 | 8.0% |
| 4-HEB(F)-F | 8.0% |
| 5-HEB(F)-F | 8.0% |
| 2-BEB(F)-C | 5.0% |
| 3-BEB(F)-C | 5.0% |
| 5-BEB(F)-C | 8.0% |
| 1O3-HB(F)-C | 6.0% |
| 3-HHEB(F)-F | 5.0% |
| 5-HHEB(F)-F | 5.0% |
| 2-HBEB(F)-C | 5.0% |
| 3-HBEB(F)-C | 6.0% |
| 5-HBEB(F)-C | 5.0% |
| 3-HBTB-2 | 10.0% |
| V2-HH-3 | 4.0% |
| V2-HHB-1 | 4.0% |

As described below, the compounds of the present invention expressed by the general formula (1) can be produced by known general methods of organic synthesis.

[Case wherein bonding group $B_1$, $B_2$, or $B_3$ represents 1,2-ethynylene group, and the ring $A_1$, $A_2$, $A_3$, or $A_4$ at one side or both sides of the bonding group represents 1,4-phenylene in which a hydrogen atom(s) may be replaced by a fluorine atom(s), or pyrimidine-2,5-diyl group, in the general formula (1)].

Compounds expressed by the general formula (1) can readily be synthesized by coupling an acetylene derivative expressed by the formula (10) and a halide expressed by the formula (11) in a solvent in the presence of a catalyst of transition metal complex and a promotor added when necessary, according to, for example, a method described in Tetrahedron Lett., vol. 22, p 305 (1981).

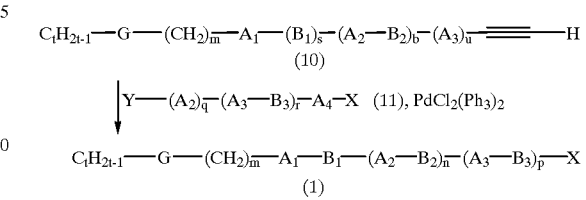

wherein G, $A_1$, $A_2$, $A_3$, $A_4$, $B_1$, $B_2$, $B_3$, X, t, m, n, and p have the same meaning as described above; q, r, s, b, and u are an integer of 0 or 1; q+b=n; r+u=p, s is 0 when n and p are 0; and Y represents a halogen atom provided that when X represents a halogen atom, then Y represents a halogen atom having higher reactivity than X.

As the complex catalyst described above, for example, a zero valent or divalent palladium complex such as dichlorobistriphenylphosphine palladium, tetrakistriphenylphosphine palladium, palladium acetate, and kahrasch complex can be mentioned. Whereas the amount of the complex catalyst to be used depends on the reactivity of substrates and is not constant, it is suitably in the range of 0.1 to 20% by mol in general, and preferably in the range of 0.5 to 5% by mol, particularly since conversion time is short and besides, side reactions hardly occur.

As the promotor, a copper salt such as copper iodide and copper bromide is preferable to increase the yield. As the solvent, while diethylamine is most suitable in general, a polar solvent such as triethylamine, pyridine, morpholine, and dimethyl formamide or a mixed solvent of one of these solvents with another suitable solvent can also be used.

While reaction temperature is suitably in the range of −40° C. to boiling point of the solvent employed, it is preferably a temperature between 0° C. and the boiling point of the solvent in particular since the catalyst activity is satisfactorily maintained and the conversion is high. Further, the reaction described above is preferably carried out in an inert gas since the active site of the catalyst is unstable against air and moisture.

When a compound of the formula (1) of the present invention is isolated after finishing of the reaction, it is particularly preferable to conduct, after ordinary treatments, purification such as distillation, recrystallization, or column chromatography to separate the catalyst remaining in the reaction mixture.

[Case wherein bonding group $B_1$, $B_2$, or $B_3$ represents a 1,2-ethynylene group, and simultaneously the ring $A_1$, $A_2$, $A_3$, or $A_4$ at both sides of the bonding group represents 1,4-cyclohexylene group or dioxane-2,5-diyl group, in the general formula (1)].

For example, the halogenated vinyl derivative expressed by the formula (14) can readily be synthesized by the known reaction of a phosphonium salt expressed by the formula (12) which can readily be prepared according to a method described in Organic Reactions, vol. 14, p 270 (1965), with an aldehyde expressed by the formula (13) which can readily be prepared according to a method described in Shin-Jikken Kagaku Kouza (Course of New Chemical Experiment), vol. 14, p 633 (1977), in a suitable solvent in the presence of a base such as potassium-t-butoxide. Objecvtive compounds of the formula (1) can readily be produced by dehydrohalogenation of a compound of the formula (14) in a suitable solvent in the presence of a base such as potassium-t-butoxide or sodium amide according to a method described in Shin-Jikken Kagaku Kouza, vol. 14, p 253 (1977).

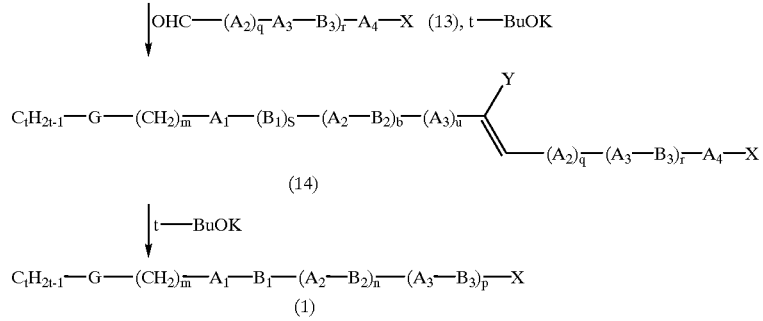

wherein G, $A_1$, $A_2$, $A_3$, $A_4$, $B_1$, $B_2$, $B_3$, X, t, m, n, and p have the same meaning as described above; q, r, s, b, and u are an integer of 0 or 1; q+b=n; r+u=p, s is 0 when n and p are 0; and Y represents a halogen atom.

After the reaction, the compound of the formula (1) can be isolated with ordinary treatments and purification such as distillation, recrystallization, or column chromatography.

Precursors (16), (18), and (22) of the formula (10) or (12) which are starting materials for compounds expressed by general formula (1) are synthesized by the following method:

[Case wherein G represents a covalent bond and a double bond exists at a terminal of an alkenyl group ($C_tH_{2t-1}$) in the general formula (1)].

For example, alkenyl compounds expressed by the formula (16) can readily be synthesized by the reaction of an aldehyde derivative expressed by the formula (15) which can readily be prepared according to a method described in Japanese Patent Publication No. Hei 4-30382 or Japanese Patent Application No. Hei 7-180745 with methyltriphenylphosphonium bromide in a suitable solvent in the presence of a base such as potassium-t-butoxide.

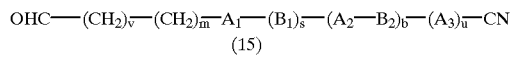

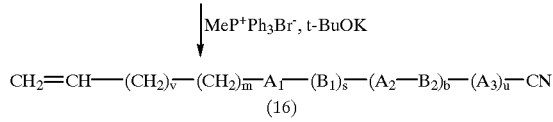

wherein $A_1$, $A_2$, $A_3$, $B_1$, $B_2$, m, s, b, and u have the same meaning as described above; v is an integer of 1 to 8; and t=v+2 wherein t has the same meaning as described above.

[Case wherein G represents a covalent bond and a double bond does not exist at a terminal of an alkenyl group ($C_tH_{2t-1}$) in the general formula (1)].

Alkenyl compounds expressed by the formula (18) can readily be synthesized by the reaction of a compound expressed by the formula (15) with diiodide expressed by the formula (17) in the presence of chrome (II) dichloride according to, for example, a method described in J. Am. Chem. Soc. vol. 109, p 951 (1987).

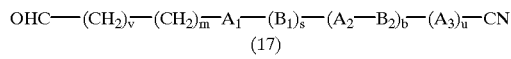

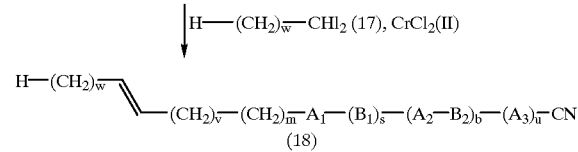

wherein $A_1$, $A_2$, $A_3$, $B_1$, $B_2$, m, s, b, and u have the same meaning as described above; v and w are an integer; and t=v+w+2 wherein t has the same meaning as described above.

[Case wherein G represents oxygen atom in the general formula (1)].

Alcohol derivatives expressed by the formula (20) can readily be synthesized by the reduction of a compound expressed by the formula (19) which can readily be prepared, for example, by a method described in Japanese Patent Publication No. Hei 4-30382 or Japanese Patent Application No. Hei 7-180745 with a reducing agent such as sodium borohydride according to, for example, a method described in J. Am. Chem. Soc., vol. 71, p 122 (1949) or ibid. vol. 74, p 3630 (1952). Then, compounds expressed by the formula (22) can readily be synthesized by reacting a compound of the formula (20) with an alkenyl halide expressed by the formula (21) in the presence of a base such as sodium hydride according to a method described in Shin-Jikken Kagaku Kouza vol. 19, p 176 (1957).

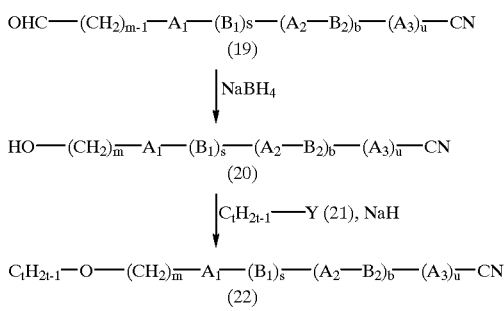

wherein $A_1$, $A_2$, $A_3$, $B_1$, $B_2$, t, m, s, b, and u have the same meaning as described above; and Y represents a halogen atom.

Compounds of the formula (16), (18), or (22) thus synthesized can readily be converted into acetylene derivatives expressed by the formula (10) according to, for example, a method described in J. Am. Chem. Soc., vol. 84, p 1745 (1962) and Tetrahedron Lett., vol. 36, p 3769 (1972), or into phosphonium salts expressed by the formula (12) according to a method described in Organic Reactions, vol. 5, p 1 (1949) and ibid., vol. 14, p 270 (1965), after converting their cyano group into aldehyde group by treating with a reducing agent such as diisobutyl aluminum hydride according to, for example, a method described in J. Org. Chem., vol. 24, p 627 (1959).

Now, the methods for producing the compounds of the present invention and use examples of the compounds will be described in more detail with reference to Examples. In each of the Examples, C indicates-crystal, N nematic phase, S smectic phase, and I isotropic liquid; and unit of every phase transition temperature is ° C.

EXAMPLE 1

Synthesis of 4-(trans-4-(3-butenyl)cyclohexyl)-4'-ethyltolan (Compound expressed by the general formula (1) wherein R represents vinyl group; G represents a covalent bond; m is 2; n is 1; p is 0; $A_1$ represents 1,4-cyclohexylene group; $A_2$ and $A_4$ represent 1,4-phenylene group; $B_1$ represents a covalent bond; $B_2$ represents 1,2-ethynylene group; and X represents ethyl group. Compound No. 49)

Degasified diethyl amine was added to a mixture of dichlorobistriphenylphosphine palladium (0.19 mmol) and copper iodide (0.03 mmol), and stirred under argon gas at room temperature for 15 min. To the mixture was added 4-ethyliodobenzene, and they were stirred at room temperature for further 30 min. To this reaction mixture was added 1-ethynyl-4-(trans-4-(3-butenyl)cyclohexyl)benzene, and they were stirred at room temperature one night. After finishing of the reaction, the solvent was distilled off, and the product was purified by column chromatography (silica gel/heptane) and then recrystallized from heptane to obtain colorless crystals (yield 89%). Various kind of spectral data of this compound well supported its structure.

Phase transition point C•58.9•S•115.1•N•175•I

EXAMPLE 2

According to the method of Example 1, 4-(trans-4-(3-butenyl)cyclohexyl)-2,6-difluoro-4'-ethyltolan (Compound No. 56) was synthesized by using 1-ethynyl-4-(trans-4-(3-butenyl)cyclohexyl)-2,6-difluorobenzene in place of 1-ethynyl-4-(trans-4-(3-butenyl)cyclohexyl)benzene.

Phase transition point C•75.1•N•174.6•I

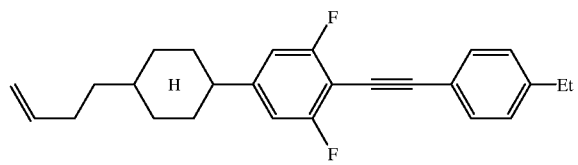

EXAMPLE 3

According to the method of Example 1, 4-(trans-4-(3-E-pentenyl)cyclohexyl)-4'-ethyltolan (Compound No. 50) was synthesized by using 1-ethynyl-4-(trans-4-(3-E-pentenyl)cyclohexyl)benzene in place of 1-ethynyl-4-(trans-4-(3-butenyl)cyclohexyl)benzene.

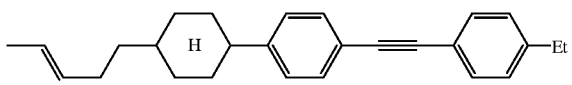

EXAMPLE 4

According to the method of Example 1, 4-(trans-4-(2-propenyloxymethyl)cyclohexyl)-4'-ethyltolan (Compound No. 63) was synthesized by using 1-ethynyl-4-(trans-4-(propenyloxymethyl)cyclohexyl)benzene in place of 1-ethynyl-4-(trans-4-(3-butenyl)cyclohexyl)benzene.

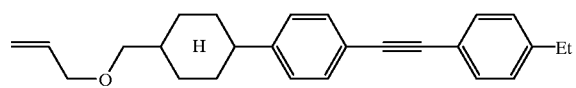

EXAMPLE 5

According to the method of Example 1, 4-(trans-4-(3-butenyl)cyclohexyl)-4'-ethoxytolan (Compound No. 64) was synthesized by using 4-ethoxyiodobenzene in place of 4-ethyliodobenzene.

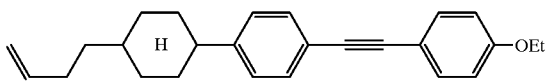

EXAMPLE 6

According to the method of Example 1, 4-(trans-4-(3-butenyl)cycloheyxl)-4'-cyanotolan (Compound No. 70) was synthesized by using 4-cyanoiodobenzene in place of 4-ethyliodobenzene.

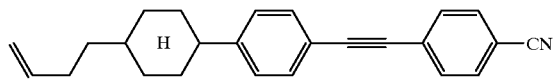

EXAMPLE 7

According to the method of Example 1, 4-(trans-4-(3-butenyl)cyclohexyl)-4'-chlorotolan (Compound No. 75) was synthesized by using 4-chloroiodobenzene in place of 4-ethyliodobenzene.

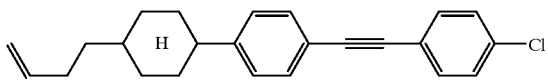

EXAMPLE 8

According to the method of Example 1, 4-(trans-4-(3-butenyl)cyclohexyl)-4'-trifluoromethyltolan (Compound No. 84) was synthesized by using 4-trifluoromethyliodobenzene in place of 4-ethyliodobenzene.

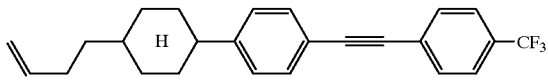

According to Examples 1 to 8 described above, the following compounds are synthesized:
Compound No. 1
  4-(3-butenyl)-4'-methyltolan
Compound No. 2
  4-(3-E-pentenyl)-4'-methyltolan
Compound No. 3
  4-(2-propenyloxymethyl)-4'-methyltolan
Compound No. 4
  4-(3-butenyl)-4'-propyltolan
Compound No. 5
  4-(3-E-pentenyl)-4'-propyltolan
Compound No. 6
  4-(3-butenyl)-4'-butyltolan
Compound No. 7
  4-(3-butenyl)-4'-pentyltolan C•28.6•N•37.2•I
Compound No. 8
  4-(3-butenyl)-2,6-difluoro-4'-methyltolan
Compound No. 9
  4-(3-E-pentenyl)-2,6-difluoro-4'-methyltolan
Compound No. 10
  4-(3-butenyl)-2,6-difluoro-4'-propyltolan
Compound No. 11
  4-(3-E-pentenyl)-2,6-difluoro-4'-propyltolan
Compound No. 12
  4-(3-butenyl)-4'-ethoxytolan
Compound No. 12-1
  4-(3-butenyl)-4'-heptoxytolan C•51.0•N•64.0•I
Compound No. 13
  4-(3-E-pentenyl)-4'-ethoxytolan
Compound No. 14
  4-(3-butenyl)-4'-cyanotolan
Compound No. 15
  4-(3-E-pentenyl)-4'-cyanotolan
Compound No. 16
  4-(3-butenyl)-3'-fluoro-4'-cyanotolan
Compound No. 17
  4-(3-E-pentenyl)-3'-fluoro-4'-cyanotolan
Compound No. 18
  4-(3-butenyl)-4'-chlorotolan
Compound No. 19
  4-(3-E-pentenyl)-4'-chlorotolan
Compound No. 20
  4-(3-butenyl)-3'-fluoro-4'-chlorotolan
Compound No. 21
  4-(3-E-pentenyl)-3'-fluoro-4'-chlorotolan
Compound No. 22
  4-(3-butenyl)-4'-bromotolan
Compound No. 23
  4-(3-E-pentenyl)-4'-bromotolan
Compound No. 24
  4-(3-butenyl)-4'-trifluoromethyltolan
Compound No. 25
  4-(3-E-pentenyl)-4'-trifluoromethyltolan
Compound No. 26
  4-(3-butenyl)-3'-fluoro-4'-trifluoromethyltolan
Compound No. 27
  4-(3-E-pentenyl)-3'-fluoro-4'-trifluoromethyltolan
Compound No. 28
  4-(3-butenyl)-4'-trifluoromethoxytolan
Compound No. 29
  4-(3-E-pentenyl)-4'-trifluoromethoxytolan
Compound No. 30
  4-(3-butenyl)-4'-(1-fluoro-2,2,2-trifluoroethyl)oxytolan
Compound No. 31
  4-(3-E-pentenyl)-4'-(1-fluoro-2,2,2-trifluoroethyl)oxytolan
Compound No. 32
  1-(trans-4-(3-butenyl)cyclohexyl)ethynyl-4-ethylbenzene
Compound No. 33
  1-(trans-4-(3-E-pentenyl)cyclohexyl)ethynyl-4-ethylbenzene
Compound No. 34
  1-(trans-4-(3-butenyl)cyclohexyl)ethynyl-4-propylbenzene
Compound No. 35
  1-(trans-4-(3-E-pentenyl)cyclohexyl)ethynyl-4-propylbenzene
Compound No. 36
  1-(trans-4-(3-butenyl)cyclohexyl)ethynyl-4-ethoxybenzene
Compound No. 37
  1-(trans-4-(3-E-pentenyl)cyclohexyl)ethynyl-4-ethoxybenzene Compound No. 38
  1-(trans-4-(3-butenyl)cyclohexyl)ethynyl-4-cyanobenzene
Compound No. 39
  1-(trans-4-(3-E-pentenyl)cyclohexyl)ethynyl-4-cyanobenzene
Compound No. 40
  1-(trans-4-(3-butenyl)cyclohexyl)ethynyl-4-chlorobenzene
Compound No. 41
  1-(trans-4-(3-E-pentenyl)cyclohexyl)ethynyl-4-chlorobenzene
Compound No. 42
  1-(trans-4-(3-butenyl)cyclohexyl)ethynyl-4-trifluoromethylbenzene
Compound No. 43
  1-(trans-4-(3-E-pentenyl)cyclohexyl)ethynyl-4-trifluoromethylbenzene
Compound No. 44
  1-(trans-4-(3-butenyl)cyclohexyl)ethynyl-4-trifluoromethoxybenzene
Compound No. 45
  1-(trans-4-(3-E-pentenyl)cyclohexyl)ethynyl-4-trifluoromethoxybenzene
Compound No. 46
  1-(trans-4-(3-butenyl)cyclohexyl)ethynyl-4-(1-fluoro-2,2,2-trifluoroethyl)oxybenzene
Compound No. 47
  1-(trans-4-(3-E-pentenyl)cyclohexyl)ethynyl-4-(1-fluoro-2,2,2-trifluoroethyl)oxybenzene
Compound No. 48
  4-(trans-4-(3-butenyl)cyclohexyl)-4'-methyltolan
Compound No. 49
  4-(trans-4-(3-butenyl)cyclohexyl)-4'-ethyltolan
Compound No. 50
  4-(trans-4-(3-E-pentenyl)cyclohexyl)-4'-ethyltolan
Compound No. 51
  4-(trans-4-(3-butenyl)cyclohexyl)-4'-propyltolan
Compound No. 52
  4-(trans-4-(3-E-pentenyl)cyclohexyl)-4'-propyltolan
Compound No. 53
  4-(trans-4-(3-butenyl)cyclohexyl)-4'-butyltolan
Compound No. 54
  4-(trans-4-(3-butenyl)cyclohexyl)-4'-pentyltolan
Compound No. 55
  4-(trans-4-(3-butenyl)cyclohexyl)-4'-(3-butenyl)tolan
Compound No. 56
  4-(trans-4-(3-butenyl)cyclohexyl)-2,6-difluoro-4'-ethyltolan
Compound No. 57
  4-(trans-4-(3-E-pentenyl)cyclohexyl)-2,6-difluoro-4'-ethyltolan
Compound No. 58
  4-(trans-4-(3-butenyl)cyclohexyl)-2,6-difluoro-4'-propyltolan
Compound No. 59
  4-(trans-4-(3-E-pentenyl)cyclohexyl)-2,6-difluoro-4'-propyltolan
Compound No. 60
  4-(trans-4-(2-propenyl)cyclohexyl)-4'-ethyltolan
Compound No. 61
  4-(trans-4-(7-octenyl)cyclohexyl)-4'-ethyltolan
Compound No. 62
  4-(trans-4-(7-E-nonenyl)cyclohexyl)-4'-ethyltolan
Compound No. 63
  4-(trans-4-(2-propenyloxymethyl)cyclohexyl)-4'-ethyltolan
Compound No. 64
  4-(trans-4-(3-butenyl)cyclohexyl)-4'-ethoxytolan
Compound No. 65
  4-(trans-4-(3-E-pentenyl)cyclohexyl)-4'-ethoxytolan
Compound No. 66
  4-(trans-4-(3-butenyl)cyclohexyl)-4'-propoxytolan
Compound No. 67
  4-(trans-4-(3-E-pentenyl)cyclohexyl)-4'-propoxytolan
Compound No. 68
  4-(trans-4-(3-butenyl)cyclohexyl)-2,6-difluoro-4'-ethoxytolan
Compound No. 69
  4-(trans-4-(3-E-pentenyl)cyclohexyl)-2,6-difluoro-4'-ethoxytolan
Compound No. 70
  4-(trans-4-(3-butenyl)cyclohexyl)-4'-cyanotolan
Compound No. 71
  4-(trans-4-(3-E-pentenyl)cyclohexyl)-4'-cyanotolan
Compound No. 72
  4-(trans-4-(3-butenyl)cyclohexyl)-2,6-difluoro-4'-cyanotolan
Compound No. 73
  4-(trans-4-(3-butenyl)cyclohexyl)-3'-fluoro-4'-cyanotolan
Compound No. 74
  4-(trans-4-(3-E-pentenyl)cyclohexyl)-3'-fluoro-4'-cyanotolan
Compound No. 75
  4-(trans-4-(3-butenyl)cyclohexyl)-4'-chlorotolan
Compound No. 76
  4-(trans-4-(3-E-pentenyl)cyclohexyl)-4'-chlorotolan
Compound No. 77
  4-(trans-4-(3-butenyl)cyclohexyl)-2,6-difluoro-4'-chlorotolan
Compound No. 78
  4-(trans-4-(3-butenyl)cyclohexyl)-3'-fluoro-4'-chlorotolan
Compound No. 79
  4-(trans-4-(3-E-pentenyl)cyclohexyl)-3'-fluoro-4'-chlorotolan
Compound No. 80
  4-(trans-4-(3-butenyl)cyclohexyl)-4'-bromotolan
Compound No. 81
  4-(trans-4-(3-E-pentenyl)cyclohexyl)-4'-bromotolan
Compound No. 82
  4-(trans-4-(3-butenyl)cyclohexyl)-3'-fluoro-4'-bromotolan
Compound No. 83
  4-(trans-4-(3-pentenyl)cyclohexyl)-3'-fluoro-4'-bromotolan
Compound No. 84
  4-(trans-4-(3-butenyl)cyclohexyl)-4'-trifluoromethyltolan
Compound No. 85
  4-(trans-4-(3-E-pentenyl)cyclohexyl)-4'-trifluoromethyltolan
Compound No. 86
  4-(trans-4-(3-butenyl)cyclohexyl)-3'-fluoro-4'-trifluoromethyltolan
Compound No. 87
  4-(trans-4-(3-E-pentenyl)cyclohexyl)-3'-fluoro-4'-trifluoromethyltolan Compound No. 88
  4-(trans-4-(3-butenyl)cyclohexyl)-4'-trifluoromethoxytolan
Compound No. 89
  4-(trans-4-(3-E-pentenyl)cyclohexyl)-4'-trifluoromethoxytolan
Compound No. 90
  4-(trans-4-(3-butenyl)cyclohexyl)-4'-(1-fluoro-2,2,2-trifluoroethyl)oxytolan
Compound No. 91
  4-(trans-4-(3-E-pentenyl)cyclohexyl)-4'-(1-fluoro-2,2,2-trifluoroethyl)oxytolan
Compound No. 92
  1-(trans-4-(trans-4-(3-butenyl)cyclohexyl)-2,5-dioxane-1-yl)ethynyl-4-ethylbenzene
Compound No. 93
  1-(trans-4-(trans-4-(3-E-pentenyl)cyclohexyl)-2,5-dioxane-1-yl)ethynyl-4-ethylbenzene
Compound No. 94
  1-(trans-4-(trans-4-(3-butenyl)cyclohexyl)-2,5-dioxane-1-yl)ethynyl-4-ethoxybenzene
Compound No. 95
  1-(trans-4-(trans-4-(3-E-pentenyl)cyclohexyl)-2,5-dioxane-1-yl)ethynyl-4-ethoxybenzene
Compound No. 96
  1-(trans-4-(trans-4-(3-butenyl)cyclohexyl)-2,5-dioxane-1-yl)ethynyl-4-cyanobenzene
Compound No. 97
  1-(trans-4-(trans-4-(3-E-pentenyl)cyclohexyl)-2,5-dioxane-1-yl)ethynyl-4-cyanobenzene
Compound No. 98
  1-(trans-4-(trans-4(3-butenyl)cyclohexyl)-2,5-dioxane-1-yl)ethynyl-4-chlorobenzene
Compound No. 99
  1-(trans-4-(trans-4-(3-E-pentenyl)cyclohexyl)-2,5-dioxane-1-yl)ethynyl-4-chlorobenzene
Compound No. 100
  1-(trans-4-(trans-4-(3-butenyl)cyclohexyl)-2,5-dioxane-1-yl)ethynyl-4-trifluoromethylbenzene
Compound No. 101
  1-(trans-4-(trans-4-(3-E-pentenyl)cyclohexyl)-2,5-dioxane-1-yl)ethynyl-4-trifluoromethylbenzene
Compound No. 102
  1-(trans-4-(trans-4-(3-butenyl)cyclohexyl)-2,5-dioxane-1-yl)ethynyl-4-trifluoromethoxybenzene
Compound No. 103
  1-(trans-4-(trans-4-(3-E-pentenyl)cyclohexyl)-2,5-dioxane-1-yl)ethynyl-4-trifluoromethoxybenzene
Compound No. 104
  1-(trans-4-(trans-4-(3-butenyl)cyclohexyl)-2,5-dioxane-1-yl)ethynyl-4-(1-fluoro-2,2,2-trifluoroethyl)oxybenzene
Compound No. 105
  1-(trans-4-(trans-4-(3-E-pentenyl)cyclohexyl)-2,5-dioxane-1-yl)ethynyl-4-(1-fluoro-2,2,2-trifluoroethyl)oxybenzene
Compound No. 106
  1-(4-(trans-4-(3-butenyl)cyclohexyl)-2,5-pyrimidine-1-yl)ethynyl-4-ethylbenzene
Compound No. 107
  1-(4-(trans-4-(3-E-pentenyl)cyclohexyl)-2,5-pyrimidine-1-yl)ethynyl-4-ethylbenzene
Compound No. 108
  1-(4-(trans-4-(3-butenyl)cyclohexyl)-2,5-pyrimidine-1-yl)ethynyl-4-ethoxybenzene
Compound No. 109
  1-(4-(trans-4-(3-E-pentenyl)cylohexyl)-2,5-pyrimidine-1-yl)ethynyl-4-ethoxybenzene
Compound No. 110
  1-(4-(trans-4-(3-butenyl)cyclohexyl)-2,5-pyrimidine-1-yl)ethynyl-4-cyanobenzene
Compound No. 111
  1-(4-(trans-4-(3-E-pentenyl)cyclohexyl)-2,5-pyrimidine-1-yl)ethynyl-4-cyanobenzene
Compound No. 112
  1-(4-(trans-4-(3-butenyl)cyclohexyl)-2,5-pyrimidine-1-yl)ethynyl-4-chlorobenzene
Compound No. 113
  1-(4-(trans-4-(3-E-pentenyl)cyclohexyl)-2,5-pyrimidine-1-yl)ethynyl-4-chlorobenzene
Compound No. 114
  1-(4-(trans-4-(3-butenyl)cyclohexyl)-2,5-pyrimidine-1-yl)ethynyl-4-trifluoromethylbenzene
Compound No. 115
  1-(4-(ttans-4-(3-E-pentenyl)cyclohexyl)-2,5-pyrimidine-1-yl)ethynyl-4-trifluoromethylbenzene
Compound No. 116
  1-(4-(trans-4-(3-butenyl)cyclohexyl)-2,5-pyrimidine-1-yl)ethynyl-4-trifluroromethylbenzene
Compound No. 117
  1-(4-(trans-4-(3-E-pentenyl)cyclohexyl)-2,5-pyrimidine-1-yl)ethynyl-4-trifluoromethoxybenzene
Compound No. 118
  1-(4-(trans-4-(3-butenyl)cyclohexyl)-2,5-pyrimidine-1-yl)ethynyl-4-(1-fluoro-2,2,2-trifluoroethyl)oxybenzene
Compound No. 119
  1-(4-(trans-4-(3-E-pentenyl)cyclohexyl)-2,5-pyrimidine-1-yl)ethynyl-4-(1-fluoro-2,2,2-trifluoroethyl)oxybenzene
Compound No. 120
  4-(2-(trans-4-(3-butenyl)cyclohexyl)ethyl)-4'-methyltolan
Compound No. 121
  4-(2-(trans-4-(3-E-pentenyl)cyclohexyl)ethyl)-4'-methyltolan
Compound No. 122
  4-(2-(trans-4-(3-butenyl)cyclohexyl)ethyl)-4'-propyltolan
Compound No. 123
  4-(2-(trans-4-(3-E-pentenyl)cyclohexyl)ethyl)-4'-propyltolan
Compound No. 124
  4-(2-(trans-4-(3-butenyl)cyclohexyl)ethyl)-2,6-difluoro-4'-methyltolan
Compound No. 125
  4-(2-(trans-4-(3-E-pentenyl)cyclohexyl)ethyl)-2,6-difluoro-4'-methyltolan
Compound No. 126
  4-(2-(trans-4-(3-butenyl)cyclohexyl)ethyl)-4'-ethoxytolan
Compound No. 127
  4-(2-(trans-4-(3-E-pentenyl)cyclohexyl)ethyl)-4'-ethoxytolan
Compound No. 128
  4-(2-(trans-4-(3-butenyl)cyclohexyl)ethyl)-4'-cyanotolan
Compound No. 129
  4-(2-(trans-4-(3-E-pentenyl)cyclohexyl)ethyl)-4'-cyanotolan Compound No. 130
  4-(2-(trans-4-(3-butenyl)cyclohexyl)ethyl)-3'-fluoro-4'-cyanotlan
Compound No. 131
  4-(2-(trans-4-(3-E-pentenyl)cyclohexyl)ethyl)-3'-fluoro-4'-cyanotolan
Compound No. 132
  4-(2-(trans-4-(3-butenyl)cyclohexyl)ethyl)-4'-chlorotolan
Compound No. 133
  4-(2-(trans-4-(3-E-pentenyl)cyclohexyl)ethyl)-4'-chlorotolan
Compound No. 134
  4-(2-(trans-4-(3-butenyl)cyclohexyl)ethyl)-4'-trifluoromethyltolan
Compound No. 135
  4-(2-(trans-4-(3-E-pentenyl)cyclohexyl)ethyl)-4'-trifluoromethyltolan
Compound No. 136
  4-(2-(trans-4-(3-butenyl)cyclohexyl)ethyl)-4'-trifluoromethoxytolan
Compound No. 137
  4-(2-(trans-4-(3-E-pentenyl)cyclohexyl)ethyl)-4'-trifluoromethoxytolan
Compound No. 138
  4-(2-(trans-4-(3-butenyl)cyclohexyl)ethyl)-4'-(1-fluoro-2,2,2-trifluoroethyl)oxytolan
Compound No. 139
  4-(2-(trans-4-(3-E-pentenyl)cyclohexyl)ethyl)-4'-(1-fluoro-2,2,2-trifluoroethyl)oxytolan
Compound No. 140
  4-(trans-4-(3-butenyl)cyclohexyl)carbonyloxy-4'-methyltolan
Compound No. 141
  4-(trans-4-(3-E-pentenyl)cyclohexyl)carbonyloxy-4'-methyltolan
Compound No. 142
  4-(trans-4-(3-butenyl)cyclohexyl)carbonyloxy-4'-propyltolan
Compound No. 143
  4-(trans-4-(3-E-pentenyl)cyclohexyl)carbonyloxy-4'-propyltolan
Compound No. 144
  4-(trans-4-(3-butenyl)cyclohexyl)carbonyloxy-2,6-difluoro-4'-methyltolan
Compound No. 145
  4-(trans-4-(3-E-pentenyl)cyclohexyl)carbonyloxy-2,6-difluoro-4'-methyltolan
Compound No. 146
  4-(trans-4-(3-butenyl)cyclohexyl)carbonyloxy-2,6-difluoro-4'-propyltolan
Compound No. 147
  4-(trans-4-(3-E-pentenyl)cyclohexyl)carbonyloxy-2,6-difluoro-4'-propyltolan
Compound No. 148
  4-(trans-4-(3-butenyl)cyclohexyl)carbonyloxy-4'-ethoxytolan
Compound No. 149
  4-(trans-4-(3-E-pentenyl)cyclohexyl)carbonyloxy-4'-ethoxytolan
Compound No. 150
  4-(trans-4-(3-butenyl)cyclohexyl)carbonyloxy-4'-cyanotolan
Compound No. 151
  4-(trans-4-(3-E-pentenyl)cyclohexyl)carbonyloxy-4'-cyanotolan
Compound No. 152
  4-(trans-4-(3-butenyl)cylohexyl)carbonyloxy-3'-fluoro-4'-cyanotolan
Compound No. 153
  4-(trans-4-(3-E-pentenyl)cyclohexyl)carbonyloxy-3'-fluoro-4'-cyanotolan
Compound No. 154
  4-(trans-4-(3-butenyl)cyclohexyl)carbonyloxy-4'-chlorotolan
Compound No. 155
  4-(trans-4-(3-E-pentenyl)cyclohexyl)carbonyloxy-4'-chlorotolan
Compound No. 156
  4-(trans-4-(3-butenyl)cyclohexyl)carbonyloxy-3'-fluoro-4'-chlorotolan
Compound No. 157
  4-(trans-4-(3-E-pentenyl)cyclohexyl)carbonyloxy-3'-fluoro-4'-chlorotolan
Compound No. 158
  4-(trans-4-(3-butenyl)cyclohexyl)carbonyloxy-4'-trifluoromethyltolan
Compound No. 159
  4-(trans-4-(3-E-pentenyl)cyclohexyl)carbonyloxy-4'-trifluoromethyltolan
Compound No. 160
  4-(trans-4-(3-butenyl)cyclohexyl)carbonyloxy-4'-trifluoromethoxytolan
Compound No. 161
  4-(trans-4-(3-E-pentenyl)cyclohexyl)carbonyloxy-4'-trifluoromethoxytolan
Compound No. 162
  4-(trans-4-(3-butenyl)cyclohexyl)carbonyloxy-4'-(1-fluoro-2,2,2-trifluoroethyl)oxytolan
Compound No. 163
  4-(trans-4-(3-E-pentenyl)cyclohexyl)carbonyloxy-4'-(1-fluoro-2,2,2-trifluoroethyl)oxytolan
Compound No. 164
  4-(4-(3-butenyl)phenyl)-4'-methyltolan
Compound No. 165
  4-(4-(3-E-pentenyl)phenyl)-4'-methyltolan
Compound No. 166
  4-(4-(2-propenyloxy)phenyl)-4'-methyltolan
Compound No. 167
  4-(4-(3-butenyl)phenyl)-4'-propyltolan
Compound No. 168 4-(4-(3-E-pentenyl)phenyl)-4'-propyltolan
Compound No. 169
  4-(4-(3-butenyl)phenyl)-2,6-difluoro-4'-methyltolan
Compound No. 170
  4-(4-(3-E-pentenyl)phenyl)-2,6-difluoro-4'-methyltolan
Compound No. 171
  4-(4-(3-butenyl)phenyl)-2,6-difluoro-4'-propyltolan
Compound No. 172
  4-(4-(3-E-pentenyl)phenyl)-2,6-difluoro-4'-propyltolan
Compound No. 173
  4-(4-(3-butenyl)phenyl)-4'-ethoxytolan
Compound No. 174
  4-(4-(3-E-pentenyl)phenyl)-4'-ethoxytolan
Compound No. 175
  4-(4-(3-butenyl)phenyl)-4'-cyanotolan Compound No. 176
  4-(4-(3-E-pentenyl)phenyl)-4'-cyanotolan
Compound No. 177
  4-(4-(3-butenyl)phenyl)-3'-fluoro-4'-cyanotolan
Compound No. 178
  4-(4-(3-E-pentenyl)phenyl)-3'-fluoro-4'-cyanotolan
Compound No. 179
  4-(4-(3-butenyl)phenyl)-4'-chlorotolan
Compound No. 180
  4-(4-(3-E-pentenyl)phenyl)-4'-chlorotolan
Compound No. 181
  4-(4-(3-butenyl)phenyl)-3'-fluoro-4'-chlorotolan
Compound No. 182
  4-(4-(3-E-pentenyl)phenyl)-3'-fluoro-4'-chlorotolan
Compound No. 183
  4-(4-(3-butenyl)phenyl)-4'-bromotolan
Compound No. 184
  4-(4-(3-E-pentenyl)phenyl)-4'-bromotolan
Compound No. 185
  4-(4-(3-butenyl)phenyl)-4'-trifluoromethyltolan
Compound No. 186
  4-(4-(3-E-pentenyl)phenyl)-4'-trifluoromethyltolan
Compound No. 187
  4-(4-(3-butenyl)phenyl)-4'-trifluoromethoxytolan
Compound No. 188
  4-(4-(3-E-pentenyl)phenyl)-4'-trifauoromethoxytolan
Compound No. 189
  4-(4-(3-butenyl)phenyl)-4'-(1-fluoro -2,2,2-trifluoroethyl)eoxytolan
Compound No. 190
  4-(4-(3-E-pentenyl)phenyl)-4'-(1-fluoro-2,2,2-trifluoroethyl)oxytolan
Compound No. 191
  trans-1-(4-(trans-4-(3-butenyl)cyclohexyl)phenyl)ethynyl-4-ethylcyclohexane
Compound No. 192
  trans-1-4-(4-(trans-4-(3-E-pentenyl)cyclohexyl)phenyl)ethynyl-4-ethyicyciohexane
Compound No. 193
  trans-1-(4-(trans-4-(3-butenyl)cyclohexyl)-2,6-difluorophenyl)ethynyl-4-ethylcyciohexane
Compound No. 194
  trans-1-4-(4-(trans-4-(3-E-pentenyl)cylohexyl)-2,6-difluorophenyl)ethynyl-4-ethylcyclohexane
Compound No. 195
  trans-1-(4-(trans-4-(3-butenyl)cyciohexyl)phenyl)ethynyl-4-ethoxycyclohexane
Compound No. 196
  trans-1-(4-(trans-4-(3-E-pentenyl)cyclohexyl)phenyl)ethynyl- 4-ethoxycyclohexane
Compound No. 197
  trans-1-(4-(trans-4-(3-butenyl)cyclohexyl)phenyl)ethynyl-4-cyanocyclohexane
Compound No. 198
  trans-1-(4-(trans-4-(3-E-pentenyl)cyclohexyl)phenyl)ethynyl-4-cyanocyclohexane
Compound No. 199
  trans-1-(4-(trans-4-(3-butenyl)cyclohexyl)phenyl)ethynyl-4-chlorocyclohexane
Compound No. 200
  trans-1-(4-(trans-4-(3-E-pentenyl)cyclohexyl)phenyl)ethynyl-4-chlorocyclohexane
Compound No. 201
  trans-1-(4-(trans-4-(3-butenyl)cyclohexyl)phenyl)ethynyl-4-bromocyclohexane
Compound No. 202
  trans-1-(4-(trans-4-(3-E-pentenyl)cyclohexyl)phenyl)ethynyl-4-bromocyclohexane
Compound No. 203
  trans-1-(4-(trans-4-(3-butenyl)cyclohexyl)phenyl)ethynyl-4-trifluoromethylcyclohexane
Compound No. 204
  trans-1-(4-(trans-4-(3-E-pentenyl)cyclohexyl)phenyl)ethynyl-4-trifluoromethylcyclohexane
Compound No. 205
  trans-1-(4-(trans-4-(3-butenyl)cyclohexyl)phenyl)ethynyl- 4-trifluoromethoxycyclohexane
Compound No. 206
  trans-1-(4-(trans-4-(3-E-pentenyl)cyclohexyl)phenyl)ethynyl-4-trifluoromethoxycyclohexane
Compound No. 207
  trans-1-(4-(trans-4-(3-butenyl)cyclohexyl)phenyl)ethynyl-4-(1-fluoro-2,2,2-trifluoroethyl)oxycyclohexane
Compound No. 208
  trans-1-(4-(trans-4-(3-E-pentenyl)cyclohexyl)phenyl)ethynyl-4-(1-fluoro-2,2,2-trifluoroethyl)oxycyclohexane
Compound No. 209
  trans-1-(4-(2-(trans-4-(3-butenyl)cyclohexyl)ethyl)phenyl)ethynyl-4-ethylcyclohexane
Compound No. 210
  trans-1-(4-(2-(trans-4-(3-E-pentenyl)cyclohexyl)ethyl)phenyl)ethynyl-4-ethylcyclohexane
Compound No. 211
  trans-1-(4-(2-(trans-4-(3-butenyl)cyclohexyl)ethyl)-2,6-difluorophenyl)ethynyl-4-ethylcyclohexane
Compound No. 212
  trans-1-(4-(2-(trans-4-(3-E-pentenyl)cyclohexyl)ethyl)-2,6-difluorophenyl)ethynyl-4-ethylcyclohexane
Compound No. 213
  trans-1-(4-(2-(trans-4-(3-butenyl)cyclohexyl)ethyl)phenyl)ethynyl-4-ethoxycyclohexane
Compound No. 214
  trans-1-(4-(2-(trans-4-(3-E-pentenyl)cyclohexyl)ethyl)phenyl)ethynyl-4-ethoxycyclohexane
Compound No. 215
  trans-1-(4-(2-(trans-4-(3-butenyl)cyclohexyl)ethyl)phenyl)ethynyl-4-cyanocyclohexane
Compound No. 216
  trans-1-(4-(2-(trans-4-(3-E-pentenyl)cyclohexyl)ethyl)phenyl)ethynyl-4-cyanocyclohexane
Compound No. 217
  trans-1-(4-(2-(trans-4-(3-butenyl)cyclohexyl)ethyl)phenyl)ethynyl-4-chlorocyclohexane
Compound No. 218
  trans-1-(4-(2-(trans-4-(3-E-pentenyl)cyclohexyl)ethyl)phenyl)ethynyl-4-chlorocyclohexane
Compound No. 219
  trans-1-(4-(2-(trans-4-(3-butenyl)cyclohexyl)ethyl)phenyl)ethynyl-4-trifluoromethylcyclohexane
Compound No. 220
  trans-1-(4-(2-(trans-4-(3-E-pentenyl)cyclohexyl)ethyl)phenyl)ethynyl-4-trifluoromethylcyclohexane
Compound No. 221
  trans-1-(4-(2-(trans-4-(3-butenyl)cyclohexyl)ethyl)phenyl)ethynyl-4-trifluoromethoxycyclohexane Compound No. 222
  trans-1-(4-(2-(trans-4-(3-E-pentenyl)cyclohexyl)ethyl)phenyl)ethynyl-4-trifluoromethoxycyclohexane
Compound No. 223
  trans-1-(4-(2-(trans-4-(3-butenyl)cyclohexyl)ethyl)phenyl)ethynyl-4-(1-fluoro-2,2,2-trifluoroethyl)oxycyclohexane
Compound No. 224
  trans-1-(4-(2-(trans-4-(3-E-pentenyl)cyclohexyl)ethyl)phenyl)ethynyl-4-(1-fluoro-2,2,2-trifluoroethyl)oxycyclohexane
Compound No. 225
  trans-1-(4-(trans-4-(3-butenyl)cyclohexylcarbonyloxy)phenyl)ethynyl-4-ethylcyclohexane
Compound No. 226
  trans-1-(4-(trans-4-(3-E-pentenyl)cyclohexylcarbonyloxy)phenyl)ethynyl-4-ethylcyclohexane
Compound No. 227
  trans-1-(4-(trans-4-(3-butenyl)cyclohexylcarbonyloxy)-2,6-difluorophenyl)ethynyl-4-ethylcyclohexane
Compound No. 228
  trans-1-(4-(trans-4-(3-E-pentenyl)cyclohexylcarbonyloxy)-2,6-difluorophenyl)ethynyl-4-ethylcyclohexane
Compound No. 229
  trans-1-(4-(trans-4-(3-butenyl)cyclohexylcarbonyloxy)phenyl)ethynyl-4-ethoxycyclohexane
Compound No. 230
  trans-1-(4-(trans-4-(3-E-pentenyl)cyclohexylcarbonyloxy)phenyl)ethynyl-4-ethoxycyclohexane
Compound No. 231
  trans-1-(4-(trans-4-(3-butenyl)cyclohexylcarbonyloxy)phenyl)ethynyl-4-cyanocyclohexane
Compound No. 232
  trans-1-(4-(trans-4-(3-E-pentenyl)cyclohexylcarbonyloxy)phenyl)ethynyl-4-cyanocyclohexane
Compound No. 233
  trans-1-(4-(trans-4-(3-butenyl)cyclohexylcarbonyloxy)phenyl)ethynyl-4-chlorocyclohexane
Compound No. 234
  trans-1-(4-(trans-4-(3-E-pentenyl)cyclohexylcarbonyloxy)phenyl)ethynyl-4-chlorocyclohexane
Compound No. 235
  trans-1-(4-(trans-4-(3-butenyl)cyclohexylcarbonyloxy)phenyl)ethynyl-4-trifluoromethylcyclohexane
Compound No. 236
  trans-1-(4-(trans-4-(3-E-pentenyl)cyclohexylcarbonyloxy)phenyl)ethynyl-4-trifluoromethylcyclohexane
Compound No. 237
  trans-1-(4-(trans-4-(3-butenyl)cyclohexylcarbonyloxy)phenyl)ethynyl-4-trifluoromethoxycyclohexane
Compound No. 238
  trans-1-(4-(trans-4-(3-E-pentenyl)cyclohexylcarbonyloxy)phenyl)ethynyl-4-trifluoromethoxycyclohexane
Compound No. 239
  trans-1-(4-(trans-4-(3-butenyl)cyclohexylcarbonyloxy)phenyl)ethynyl-4-(1-fluoro-2,2,2-trifluoroethyl)oxycyclohexane
Compound No. 240
  trans-1-(4-(trans-4-(3-E-pentenyl)cyclohexylcarbonyloxy)phenyl)ethynyl-4-(1-fluoro-2,2,2-trifluoroethyl)oxycyclohexane
Compound No. 241
  trans-1-(4-(4-(3-butenyl)phenyl)phenyl)ethynyl-4-ethylcyclohexane
Compound No. 242
  trans-1-(4-(4-(3-E-pentenyl)phenyl)phenyl)ethynyl-4-ethylcyclohexane
Compound No. 243
  trans-1-(4-(4-(2-propenyloxy)phenyl)phenyl)ethynyl-4-ethynylcyclohexane
Compound No. 244
  trans-1-(4-(4-(3-butenyl)phenyl)-2,6-difluorophenyl)ethynyl-4-ethylcyclohexane
Compound No. 245
  trans-1-(4-(4-(3-E-pentenyl)phenyl)-2,6-difluorophenyl)ethynyl-4-ethylcyclohexane
Compound No. 246
  trans-1-(4-(4-(3-butenyl)phenyl)phenyl)ethynyl-4-ethoxycyclohexane
Compound No. 247
  trans-1-(4-(4-(3-E-pentenyl)phenyl)phenyl)ethynyl-4-ethoxycyclohexane
Compound No. 248
  trans-1-(4-(4-(3-butenyl)phenyl)phenyl)ethynyl-4-cyanocyclohexane
Compound No. 249
  trans-1-(4-(4-(3-E-pentenyl)phenyl)phenyl)ethynyl-4-cyanocyclohexane
Compound No. 250
  trans-1-(4-(4-(3-butenyl)phenyl)phenyl)ethynyl-4-chlorocyclohexane
Compound No. 251
  trans-1-(4-(4-(3-E-pentenyl)phenyl)phenyl)ethynyl-4-chlorocyclohexane
Compound No. 252
  trans-1-(4-(4-(3-butenyl)phenyl)phenyl)ethynyl-4-trifluoromethylcyclohexane
Compound No. 253
  trans-1-(4-(4-(3-E-pentenyl)phenyl)phenyl)ethynyl-4-trifluoromethylcyclohexane
Compound No. 254
  trans-1-(4-(4-(3-butenyl)phenyl)phenyl)ethynyl-4-trifluoromethoxycyclohexane
Compound No. 255
  trans-1-(4-(4-(3-E-pentenyl)phenyl)phenyl)ethynyl-4-trifluoromethoxycyclohexane
Compound No. 256
  trans-1-(4-(4-(3-butenyl)phenyl)phenyl)ethynyl-4-(1-fluoro-2,2,2-trifluoroethyl)oxycyclohexane
Compound No. 257
  trans-1-(4-(4-(3-E-pentenyl)phenyl)phenyl)ethynyl-4-(1-fluoro-2,2,2-trifluoroethyl)oxycyclohexane
Compound No. 258
  4-(3-butenyl)-4'-(trans-4-propylcyclohexyl)tolan
Compound No. 258-1
  4-(3-butenyl)-4'-(trans-4-pentylcyclohexyl)tolan
  C•63.1•S•112.6•N•190.9•I
Compound No. 259
  trans-1-(4-(3-butenyl)phenyl)ethynyl-4-(4-ethylphenyl)cyclohexane Compound No. 260
  trans-1-(4-(3-E-pentenyl)phenyl)ethynyl-4-(4-ethylphenyl)cyclohexane
Compound No. 261
  trans-1-(4-(3-butenyl)-2,6-difluorophenyl)ethynyl-4-(4-ethylphenyl)cyclohexane
Compound No. 262
  trans-1-(4-(3-E-pentenyl)-2,6-difluorophenyl)ethynyl-4-(4-ethylphenyl)cyclohexane
Compound No. 263
  trans-1-(4-(3-butenyl)phenyl)ethynyl-4-(4-ethoxyphenyl)cyclohexane
Compound No. 264
  trans-1-(4-(3-E-pentenyl)phenyl)ethynyl-4-(4-ethoxyphenyl)cyclohexane
Compound No. 265
  trans-1-(4-(3-butenyl)phenyl)ethynyl-4-(4-cyanophenyl)cyclohexane
Compound No. 266
  trans-1-(4-(3-E-pentenyl)phenyl)ethynyl-4-(4-cyanophenyl)cyclohexane
Compound No. 267
  trans-1-(4-(3-butenyl)phenyl)ethynyl-4-(4-chlorophenyl)cyclohexane
Compound No. 268
  trans-1-(4-(3-E-pentenyl)phenyl)ethynyl-4-(4-chlorophenyl)cyclohexane
Compound No. 269
  trans-1-(4-(3-butenyl)phenyl)ethynyl-4-(4-trifluoromethylphenyl)cyclohexane
Compound No. 270
  trans-1-(4-(3-E-pentenyl)phenyl)ethynyl-4-(4-trifluoromethylphenyl)cyclohexane
Compound No. 271
  trans-1-(4-(3-butenyl)phenyl)ethynyl-4-(4-trifluoromethoxyphenyl)cyclohexane
Compound No. 272
  trans-1-(4-(3-E-pentenyl)phenyl)ethynyl-4-(4-trifluoromethoxyphenyl)cyclohexane
Compound No. 273
  trans-1-(4-(3-butenyl)phenyl)ethynyl-4-(4-(1-fluoro-2,2,2-trifluoroethyl)oxyphenyl)cyclohexane
Compound No. 274
  trans-1-(4-(3-E-pentenyl)phenyl)ethynyl-4-(4-(1-fluoro-2,2,2-trifluoroethyl)oxyphenyl)cyclohexane
Compound No. 275
  4-(trans-4-(trans-4-(3-butenyl)cyclohexyl)cyclohexyl)-4'-methyltolan
Compound No. 276
  4-(trans-4-(trans-4-(3-E-pentenyl)cyclohexyl)cyclohexyl)-4'-methyltolan
Compound No. 277
  4-(trans-4-(trans-4-(3-butenyl)cyclohexyl)cyclohexyl)-4'-propyltolan
Compound No. 278
  4-(trans-4-(trans-4-(3-E-pentenyl)cyclohexyl)cyclohexyl)-4'-propyltolan
Compound No. 279
  4-(trans-4-(trans-4-(3-butenyl)cyclohexyl)cyclohexyl)-4'-butyltolan
Compound No. 280
  4-(trans-4-(trans-4-(3-butenyl)cyclohexyl)cyclohexyl)-4'-pentyltolan
Compound No. 281
  4-(trans-4-(trans-4-(3-butenyl)cyclohexyl)cyclohexyl)-2,6-difluoro-4'-methyltolan
Compound No. 282
  4-(trans-4-(trans-4-(3-E-pentenyl)cyclohexyl)cyclohexyl)-2,6-difluoro-4'-methyltolan
Compound No. 283
  4-(trans-4-(trans-4-(3-butenyl)cyclohexyl)cyclohexyl)-2,6-difluoro-4'-propyltolan
Compound No. 284
  4-(trans-4-(trans-4-(3-E-pentenyl)cyclohexyl)cyclohexyl)-2,6-difluoro-4'-propyltolan
Compound No. 285
  4-(trans-4-(trans-4-(2-propenyloxymethyl)cyclohexyl)cyclohexyl)-4'-ethyltolan
Compound No. 286
  4-(trans-4-(trans-4-(3-butenyl)cyclohexyl)cyclohexyl)-4'-ethoxytolan
Compound No. 287
  4-(trans-4-(trans-4-(3-E-pentenyl)cyclohexyl)cyclohexyl)-4'-ethoxytolan
Compound No. 288
  4-(trans-4-(trans-4-(3-butenyl)cyclohexyl)cyclohexyl)-4'-propoxytolan
Compound No. 289
  4-(trans-4-(trans-4-(3-E-pentenyl)cyclohexyl)cyclohexyl)-4'-propoxytolan
Compound No. 290
  4-(trans-4-(trans-4-(3-butenyl)cyclohexyl)cyclohexyl)-4'-cyanotolan
Compound No. 291
  4-(trans-4-(trans-4-(3-E-pentenyl)cyclohexyl)cyclohexyl)-4'-cyanotolan
Compound No. 292
  4-(trans-4-(trans-4-(3-butenyl)cyclohexyl)cyclohexyl)-3'-fluoro-4'-cyanotolan
Compound No. 293
  4-(trans-4-(trans-4-(3-E-pentenyl)cyclohexyl)cyclohexyl)-3'-fluoro-4'-cyanotolan
Compound No. 294
  4-(trans-4-(trans-4-(3-butenyl)cyclohexyl)cyclohexyl)-4'-chlorotolan
Compound No. 295
  4-(trans-4-(trans-4-(3-E-pentenyl)cyclohexyl)cyclohexyl)-4'-chlorotolan
Compound No. 296
  4-(trans-4-(trans-4-(3-butenyl)cyclohexyl)cyclohexyl)-3'-fluoro-4'-chlorotolan
Compound No. 297
  4-(trans-4-(trans-4-(3-E-pentenyl)cyclohexyl)cyclohexyl)-3'-fluoro-4'-chlorotolan
Compound No. 298
  4-(trans-4-(trans-4-(3-butenyl)cyclohexyl)cyclohexyl)-4'-bromotolan
Compound No. 299
  4-(trans-4-(trans-4-(3-E-pentenyl)cyclohexyl)cyclohexyl)-4'-bromotolan
Compound No. 300
  4-(trans-4-(trans-4-(3-butenyl)cyclohexyl)cyclohexyl)-4'-trifluoromethyltolan
Compound No. 301
  4-(trans-4-(trans-4-(3-E-pentenyl)cyclohexyl)cyclohexyl)-4'-trifluoromethyltolan Compound No. 302
  4-(trans-4-(trans-4-(3-butenyl)cyclohexyl)cyclohexyl)-4'-trifluoromethoxytolan
Compound No. 303
  4-(trans-4-(trans-4-(3-E-pentenyl)cyclohexyl)cyclohexyl)-4'-trifluoromethoxytolan
Compound No. 304
  4-(trans-4-(trans-4-(3-butenyl)cyclohexyl)cyclohexyl)-4'-(1-fluoro-2,2,2-trifluoroethyl)oxytolan
Compound No. 305
  4-(trans-4-(trans-4-(3-E-pentenyl)cyclohexyl)cyclohexyl)-4'-(1-fluoro-2,2,2-trifluoroethyl)oxytolan
Compound No. 306
  4-(trans-4-(2-(trans-4-(3-butenyl)cyclohexyl)ethyl)cyclohexyl)-4'-methyltolan
Compound No. 307
  4-(trans-4-(2-(trans-4-(3-E-pentenyl)cyclohexyl)ethyl)cyclohexyl)-4'-methyltolan
Compound No. 308
  4-(trans-4-(2-(trans-4-(3-butenyl)cyclohexyl)ethyl)cyclohexyl)-4'-propyltolan
Compound No. 309
  4-(trans-4-(2-(trans-4-(3-E-pentenyl)cyclohexyl)ethyl)cyclohexyl)-4'-propyltolan
Compound No. 310
  4-(trans-4-(2-(trans-4-(3-butenyl)cyclohexyl)ethyl)cyclohexyl)-2,6-difluoro-4'-methyltolan
Compound No. 311
  4-(trans-4-(2-(trans-4-(3-E-pentenyl)cyclohexyl)ethyl)cyclohexyl)-2,6-difluoro-4'-methyltolan
Compound No. 312
  4-(trans-4-(2-(trans-4-(3-butenyl)cyclohexyl)ethyl)cyclohexyl)-2,6-difluoro-4'-propyltolan
Compound No. 313
  4-(trans-4-(2-(trans-4-(3-E-pentenyl)cyclohexyl)ethyl)cyclohexyl)-2,6-difluoro-4'-propyltolan
Compound No. 314
  4-(trans-4-(2-(trans-4-(3-butenyl)cyclohexyl)ethyl)cyclohexyl)-4'-ethoxytolan
Compound No. 315
  4-(trans-4-(2-(trans-4-(3-E-pentenyl)cyclohexyl)ethyl)cyclohexyl)-4'-ethoxytolan
Compound No. 316
  4-(trans-4-(2-(trans-4-(3-butenyl)cyclohexyl)ethyl)cyclohexyl)-4'-propoxytolan
Compound No. 317
  4-(trans-4-(2-(trans-4-(3-E-pentenyl)cyclohexyl)ethyl)cyclohexyl)-4'-propoxytolan
Compound No. 318
  4-(trans-4-(2-(trans-4-(3-butenyl)cyclohexyl)ethyl)cyclohexyl)-4'-cyanotolan
Compound No. 319
  4-(trans-4-(2-(trans-4-(3-E-pentenyl)cyclohexyl)ethyl)cyclohexyl)-4'-cyanotolan
Compound No. 320
  4-(trans-4-(2-(trans-4-(3-butenyl)cyclohexyl)ethyl)cyclohexyl)-3'-fluoro-4'-cyanotolan
Compound No. 321
  4-(trans-4-(2-(trans-4-(3-E-pentenyl)cyclohexyl)ethyl)cyclohexyl)-3'-fluoro-4'-cyanotolan
Compound No. 322
  4-(trans-4-(2-(trans-4-(3-butenyl)cyclohexyl)ethyl)cyclohexyl)-4'-chlorotolan
Compound No. 323
  4-(trans-4-(2-(trans-4-(3-E-pentenyl)cyclohexyl)ethyl)cyclohexyl)-4'-chlorotolan
Compound No. 324
  4-(trans-4-(2-(trans-4-(3-butenyl)cyclohexyl)ethyl)cyclohexyl)-3'-fluoro-4'-chlorotolan
Compound No. 325
  4-(trans-4-(2-(trans-4-(3-E-pentenyl)cyclohexyl)ethyl)cyclohexyl)-3'-fluoro-4'-chlorotolan
Compound No. 326
  4-(trans-4-(2-(trans-4-(3-butenyl)cyclohexyl)ethyl)cyclohexyl)-4'-bromotolan
Compound No. 327
  4-(trans-4-(2-(trans-4-(3-E-pentenyl)cyclohexyl)ethyl)cyclohexyl)-4'-bromotolan
Compound No. 328
  4-(trans-4-(2-(trans-4-(3-butenyl)cyclohexyl)ethyl)cyclohexyl)-4'-trifluoromethyltolan
Compound No. 329
  4-(trans-4-(2-(trans-4-(3-E-pentenyl)cyclohexyl)ethyl)cyclohexyl)-4'-trifluoromethyltolan
Compound No. 330
  4-(trans-4-(2-(trans-4-(3-butenyl)cyclohexyl)ethyl)cyclohexyl)-4'-trifluoromethoxytolan
Compound No. 331
  4-(trans-4-(2-(trans-4-(3-E-pentenyl)cyclohexyl)ethyl)cyclohexyl)-4'-trifluoromethoxytolan
Compound No. 332
  4-(trans-4-(2-(trans-4-(3-butenyl)cyclohexyl)ethyl)cyclohexyl)-4'-(1-fluoro-2,2,2-trifluoroethyl)oxytolan
Compound No. 333
  4-(trans-4-(2-(trans-4-(3-E-pentenyl)cyclohexyl)ethyl)cyclohexyl)-4'-(1-fluoro-2,2,2-trifluoroethyl)oxytolan
Compound No. 334
  4-(4-(trans-4-(3-butenyl)cyclohexyl)phenyl)-4'-methyltolan
Compound No. 335
  4-(4-(trans-4-(3-E-pentenyl)cyclohexyl)phenyl)-4'-methyltolan
Compound No. 336
  4-(4-(trans-4-(3-butenyl)cyclohexyl)phenyl)-4'-propyltolan
Compound No. 337
  4-(4-(trans-4-(3-E-pentenyl)cyclohexyl)phenyl)-4'-propyltolan
Compound No. 338
  4-(4-(trans-4-(3-butenyl)cyclohexyl)phenyl)-2,6-difluoro-4'-methyltolan
Compound No. 339
  4-(4-(trans-4-(3-E-pentenyl)cyclohexyl)phenyl)-2,6-difluoro-4'-methyltolan
Compound No. 340
  4-(4-(trans-4-(3-butenyl)cyclohexyl)phenyl)-2,6-difluoro- 4'-propyltolan
Compound No. 341
  4-(4-(trans-4-(3-E-pentenyl)cyclohexyl)phenyl)-2,6-difluoro-4'-propyltolan
Compound No. 342
  4-(4-(trans-4-(3-butenyl)cyclohexyl)phenyl)-4'-ethoxytolan
Compound No. 343
  4-(4-(trans-4-(3-E-pentenyl)cyclohexyl)phenyl)-4'-ethoxytolan Compound No. 344
  4-(4-(trans-4-(3-butenyl)cyclohexyl)phenyl)-4'-propoxytolan
Compound No. 345
  4-(4-(trans-4-(3-E-pentenyl)cyclohexyl)phenyl)-4'-propoxytolan
Compound No. 346
  4-(4-(trans-4-(3-butenyl)cyclohexyl)phenyl)-4'-cyanotolan
Compound No. 347
  4-(4-(trans-4-(3-E-pentenyl)cyclohexyl)phenyl)-4'-cyanotolan
Compound No. 348
  4-(4-(trans-4-(3-butenyl)cyclohexyl)phenyl)-3'-fluoro-4'-cyanotolan
Compound No. 349
  4-(4-(trans-4-(3-E-pentenyl)cyclohexyl)phenyl)-3'-fluoro-4'-cyanotolan
Compound No. 350
  4-(4-(trans-4-(3-butenyl)cyclohexyl)phenyl)-4'-chlorotolan
Compound No. 351
  4-(4-(trans-4-(3-E-pentenyl)cyclohexyl)phenyl)-4'-chlorotolan
Compound No. 352
  4-(4-(trans-4-(3-butenyl)cyclohexyl)phenyl)-3'-fluoro-4'-chlorotolan
Compound No. 353
  4-(4-(trans-4-(3-E-pentenyl)cyclohexyl)phenyl)-3'-fluoro-4'-chlorotolan
Compound No. 354
  4-(4-(trans-4-(3-butenyl)cyclohexyl)phenyl)-4'-bromotolan
Compound No. 355
  4-(4-(trans-4-(3-E-pentenyl)cyclohexyl)phenyl)-4'-bromotolan
Compound No. 356
  4-(4-(trans-4-(3-butenyl)cyclohexyl)phenyl)-4'-trifluoromethyltolan
Compound No. 357
  4-(4-(trans-4-(3-E-pentenyl)cyclohexyl)phenyl)-4'-trifluoromethyltolan
Compound No. 358
  4-(4-(trans-4-(3-butenyl)cyclohexyl)phenyl)-4'-trifluoromethoxytolan
Compound No. 359
  4-(4-(trans-4-(3-E-pentenyl)cyclohexyl)phenyl)-4'-trifluoromethoxytolan
Compound No. 360
  4-(4-(trans-4-(3-butenyl)cyclohexyl)phenyl)-4'-(1-fluoro-2,2,2-trifluoroethyl)oxytolan
Compound No. 361
  4-(4-(trans-4-(3-E-pentenyl)cyclohexyl)phenyl)-4'-(1-fluoro-2,2,2-trifluoroethyl)oxytolan
Compound No. 362
  4-(4-(2-(trans-4-(3-butenyl)cyclohexyl)ethyl)phenyl)-4'-methyltolan
Compound No. 363
  4-(4-(2-(trans-4-(3-E-pentenyl)cyclohexyl)ethyl)phenyl)-4'-methyltolan
Compound No. 364
  4-(4-(2-(trans-4-(3-butenyl)cyclohexyl)ethyl)phenyl)-4'-propyltolan
Compound No. 365
  4-(4-(2-(trans-4-(3-E-pentenyl)cyclohexyl)ethyl)phenyl)-4'-propyltolan
Compound No. 366
  4-(4-(2-(trans-4-(3-butenyl)cyclohexyl)ethyl)phenyl)-2,6-difluoro-4'-methyltolan
Compound No. 367
  4-(4-(2-(trans-4-(3-E-pentenyl)cyclohexyl)ethyl)phenyl)-2,6-difluoro-4'-methyltolan
Compound No. 368
  4-(4-(2-(trans-4-(3-butenyl)cyclohexyl)ethyl)phenyl)-2,6-difluoro-4'-propyltolan
Compound No. 369
  4-(4-(2-(trans-4-(3-E-pentenyl)cyclohexyl)ethyl)phenyl)-2,6-difluoro-4'-propyltolan
Compound No. 370
  4-(4-(2-(trans-4-(3-butenyl)cyclohexyl)ethyl)phenyl)-4'-ethoxytolan
Compound No. 371
  4-(4-(2-(trans-4-(3-E-pentenyl)cyclohexyl)ethyl)phenyl)-2,6-difluoro-4'-ethoxytolan
Compound No. 372
  4-(4-(2-(trans-4-(3-butenyl)cyclohexyl)ethyl)phenyl)-4'-propoxytolan
Compound No. 373
  4-(4-(2-(trans-4-(3-E-pentenyl)cyclohexyl)ethyl)phenyl)-2,6-difluoro-4'-propoxytolan
Compound No. 374
  4-(4-(2-(trans-4-(3-butenyl)cyclohexyl)ethyl)phenyl)-4'-cyanotolan
Compound No. 375
  4-(4-(2-(trans-4-(3-E-pentenyl)cyclohexyl)ethyl)phenyl)-4'-cyanotolan
Compound No. 376
  4-(4-(2-(trans-4-(3-butenyl)cyclohexyl)ethyl)phenyl)-3'-fluoro-4'-cyanotolan
Compound No. 377
  4-(4-(2-(trans-4-(3-E-pentenyl)cyclohexyl)ethyl)phenyl)-3'-fluoro-4'-cyanotolan
Compound No. 378
  4-(4-(2-(trans-4-(3-butenyl)cyclohexyl)ethyl)phenyl)-4'-chlorotolan
Compound No. 379
  4-(4-(2-(trans-4-(3-E-pentenyl)cyclohexyl)ethyl)phenyl)-4'-chlorotolan
Compound No. 380
  4-(4-(2-(trans-4-(3-butenyl)cyclohexyl)ethyl)phenyl)-3'-fluoro-4'-chlorotolan
Compound No. 381
  4-(4-(2-(trans-4-(3-E-pentenyl)cyclohexyl)ethyl)phenyl)-3'-fluoro-4'-chlorotolan
Compound No. 382
  4-(4-(2-(trans-4-(3-butenyl)cyclohexyl)ethyl)phenyl)-4'-bromotolan
Compound No. 383
  4-(4-(2-(trans-4-(3-E-pentenyl)cyclohexyl)ethyl)phenyl)-4'-bromotolan
Compound No. 384
  4-(4-(2-(trans-4-(3-butenyl)cyclohexyl)ethyl)phenyl)-4'-trifluoromethyltolan
Compound No. 385
  4-(4-(2-(trans-4-(3-E-pentenyl)cyclohexyl)ethyl)phenyl)-4'-trifluoromethyltolan Compound No. 386
  4-(4-(2-(trans-4-(3-butenyl)cyclohexyl)ethyl)phenyl)-4'-trifluoromethoxytolan
Compound No. 387
  4-(4-(2-(trans-4-(3-E-pentenyl)cyclohexyl)ethyl)phenyl)-4'-trifluoromethoxytolan
Compound No. 388
  4-(4-(2-(trans-4-(3-butenyl)cyclohexyl)ethyl)phenyl)-4'-(1-fluoro-2,2,2-trifluoroethyl)oxytolan
Compound No. 389
  4-(4-(2-(trans-4-(3-E-pentenyl)cyclohexyl)ethyl)phenyl)-4'-(1-fluoro-2,2,2-trifluoroethyl)oxytolan
Compound No. 390
  4-(trans-4-(4-(3-butenyl)phenyl)cyclohexyl)-4'-methyltolan
Compound No. 391
  4-(trans-4-(4-(3-E-pentenyl)phenyl)cyclohexyl)-4'-methyltolan
Compound No. 392
  4-(trans-4-(4-(3-butenyl)phenyl)cyclohexyl)-4'-propyltolan
Compound No. 393
  4-(trans-4-(4-(3-E-pentenyl)phenyl)cyclohexyl)-4'-propyltolan
Compound No. 394
  4-(trans-4-(4-(3-butenyl)phenyl)cyclohexyl)-2,6-difluoro-4'-methyltolan
Compound No. 395
  4-(trans-4-(4-(3-E-pentenyl)phenyl)cyclohexyl)-2,6-difluoro-4'-methyltolan
Compound No. 396
  4-(trans-4-(4-(3-butenyl)phenyl)cyclohexyl)-2,6-difluoro-4'-propyltolan
Compound No. 397
  4-(trans-4-(4-(3-E-pentenyl)phenyl)cyclohexyl)-2,6-difluoro-4'-propyltolan
Compound No. 398
  4-(trans-4-(4-(3-butenyl)phenyl)cyclohexyl)-4'-ethoxytolan
Compound No. 399
  4-(trans-4-(4-(3-E-pentenyl)phenyl)cyclohexyl)-4'-ethoxytolan
Compound No. 400
  4-(trans-4-(4-(3-butenyl)phenyl)cyclohexyl)-4'-propoxytolan
Compound No. 401
  4-(trans-4-(4-(3-E-pentenyl)phenyl)cyclohexyl)-4'-propoxytolan
Compound No. 402
  4-(trans-4-(4-(3-butenyl)phenyl)cyclohexyl)-4-cyanotolan
Compound No. 403
  4-(trans-4-(4-(3-E-pentenyl)phenyl)cyclohexyl)-4'-cyanotolan
Compound No. 404
  4-(trans-4-(4-(3-butenyl)phenyl)cyclohexyl)-3'-fluoro-4'-cyanotolan
Compound No. 405
  4-(trans-4-(4-(3-E-pentenyl)phenyl)cyclohexyl)-3'-fluoro-4'-cyanotolan
Compound No. 406
  4-(trans-4-(4-(3-butenyl)phenyl)cyclohexyl)-4'-chlorotolan
Compound No. 407
  4-(trans-4-(4-(3-E-pentenyl)phenyl)cyclohexyl)-4'-chlorotolan
Compound No. 408
  4-(trans-4-(4-(3-butenyl)phenyl)cyclohexyl)-3'-fluoro-4'-chlorotolan
Compound No. 409
  4-(trans-4-(4-(3-E-pentenyl)phenyl)cyclohexyl)-3'-fluoro-4'-chlorotolan
Compound No. 410
  4-(trans-4-(4-(3-butenyl)phenyl)cyclohexyl)-4'-bromotolan
Compound No. 411
  4-(trans-4-(4-(3-E-pentenyl)phenyl)cyclohexyl)-4'-bromotolan
Compound No. 412
  4-(trans-4-(4-(3-butenyl)phenyl)cyclohexyl)-4'-trifluoromethyltolan
Compound No. 413
  4-(trans-4-(4-(3-E-pentenyl)phenyl)cyclohexyl)-4'-trifluoromethyltolan
Compound No. 414
  4-(trans-4-(4-(3-butenyl)phenyl)cyclohexyl)-4'-trifluoromethoxytolan
Compound No. 415
  4-(trans-4-(4-(3-E-pentenyl)phenyl)cyclohexyl)-4'-trifluoromethoxytolan
Compound No. 416
  4-(trans-4-(4-(3-butenyl)phenyl)cyclohexyl)-4'-(1-fluoro-2,2,2-trifluoro ethyl)oxytolan
Compound No. 417
  4-(trans-4-(4-(3-E-pentenyl)phenyl)cyclohexyl)-4'-(1-fluoro-2,2,2-trifluoroethyl)oxytolan
Compound No. 418
  4-(4-(3-butenyl)phenylethynyl)phenyl)-4'-methyltolan
Compound No. 419
  4-(4-(3-E-pentenyl)phenylethynyl)phenyl)-4'-methyltolan
Compound No. 420
  4-(4-(3-butenyl)phenylethynyl)phenyl)-4'-propyltolan
Compound No. 421
  4-(4-(3-E-pentenyl)phenylethynyl)phenyl)-4'-propyltolan
Compound No. 422
  4-(4-(3-butenyl)phenylethynyl)phenyl)-2,6-difluoro-4'-methyltolan
Compound No. 423
  4-(4-(3-E-pentenyl)phenylethynyl)phenyl)-2,6-difluoro-4'-methyltolan t
Compound No. 424
  4-(4-(3-butenyl)phenylethynyl)phenyl)-2,6-difluoro-4'-propyltolan
Compound No. 425
  4-(4-(3-E-pentenyl)phenylethynyl)phenyl)-2,6-difluoro-4'-propyltolan
Compound No. 426
  4-(4-(3-butenyl)-2,6-difluorophenylethynyl)phenyl)-4'-methyltolan
Compound No. 427
  4-(4-(3-E-pentenyl)-2,6-difluorophenylethynyl)phenyl)-4'-methyltolan
Compound No. 428
  4-(4-(3-butenyl)-2,6-difluorophenylethynyl)phenyl)-4'-propyltolan Compound No. 429
  4-(4-(4-(3-E-pentenyl)-2,6-difluorophenylethynyl)phenyl)-4'-propyltolan
Compound No. 430
  4-(4-(4-(3-butenyl)-2,6-difluorophenylethynyl)phenyl)-2,6-difluoro-4'-methyltolan
Compound No. 431
  4-(4-(4-(3-E-pentenyl)-2,6-difluorophenylethynyl)phenyl)-2,6-difluoro-4'-methyltolan
Compound No. 432
  4-(4-(4-(3-butenyl)-2,6-difluorophenylethynyl)phenyl)-2,6-difluoro-4'-propyltolan
Compound No. 433
  4-(4-(4-(3-E-pentenyl)-2,6-difluorophenylethynyl)phenyl)-2,6-difluoro-4'-propyltolan
Compound No. 434
  4-(4-(4-(3-butenyl)phenylethynyl)phenyl)-4'-ethoxytolan
Compound No. 435
  4-(4-(4-(3-E-pentenyl)phenylethynyl)phenyl)-4'-ethoxytolan
Compound No. 436
  4-(4-(4-(3-butenyl)phenylethynyl)phenyl)-4'-propoxytolan
Compound No. 437
  4-(4-(4-(3-E-pentenyl)phenylethynyl)phenyl)-4'-propoxytolan
Compound No. 438
  4-(4-(4-(3-butenyl)phenylethynyl)phenyl)-4'-cyanotolan
Compound No. 439
  4-(4-(4-(3-E-pentenyl)phenylethynyl)phenyl)-4'-cyanotolan
Compound No. 440
  4-(4-(4-(3-butenyl)phenylethynyl)phenyl)-3'-fluoro-4'-cyanotolan
Compound No. 441
  4-(4-(4-(3-E-pentenyl)phenylethynyl)phenyl)-3'-fluoro-4'-cyanotolan
Compound No. 442
  4-(4-(4-(3-butenyl)phenylethynyl)phenyl)-4'-chlorotolan
Compound No. 443
  4-(4-(4-(3-E-pentenyl)phenylethynyl)phenyl)-4'-chlorotolan
Compound No. 444
  4-(4-(4-(3-butenyl)phenylethynyl)phenyl)-3'-fluoro-4'-chlorotolan
Compound No. 445
  4-(4-(4-(3-E-pentenyl)phenylethynyl)phenyl)-3'-fluoro-4'-chlorotolan
Compound No. 446
  4-(4-(4-(3-butenyl)phenylethynyl)phenyl)-4'-bromotolan
Compound No. 447
  4-(4-(4-(3-E-pentenyl)phenylethynyl)phenyl)-4'-bromotolan
Compound No. 448
  4-(4-(4-(3-butenyl)phenylethynyl)phenyl)-4'-trifluoromethyltolan
Compound No. 449
  4-(4-(4-(3-E-pentenyl)phenylethynyl)phenyl)-4'-trifluoromethyltolan
Compound No. 450
  4-(4-(4-(3-butenyl)phenylethynyl)phenyl)-4'-trifluoromethoxytolan
Compound No. 451
  4-(4-(4-(3-E-pentenyl)phenylethynyl)phenyl)-4'-trifluoromethoxytolan
Compound No. 452
  4-(4-(4-(3-butenyl)phenylethynyl)phenyl)-4'-(1-fluoro-2,2,2-trifluoroethyl)oxytolan
Compound No. 453
  4-(4-(4-(3-E-pentenyl)phenylethynyl)phenyl)-4'-(1-fluoro-2,2,2-trifluoroethyl)oxytolan EXAMPLE 9 (Use Example 1)

Nematic liquid crystal of a liquid crystal composition comprising
  4-(trans-4-propylcyclohexyl)benzonitrile 24% (% by weight, the same will be applied in the followings)
  4-(trans-4-pentylcyclohexyl)benzonitrile 36%
  4-(trans-4-heptylcyclohexyl)benzonitrile 25%, and
  4-(4-propylphenyl)benzonitrile 15%
had a clearing point ($T_{NI}$) of 71.7° C. When this liquid crystal composition was filled in a TN cell (twisted nematic cell) having a thickness of 9 μm, its operation threshold voltage was 1.78 V, value of dielectric anisotropy ($\Delta\epsilon$) was +11.0, value of optical anisotropy ($\Delta n$) was 0.137, and viscosity at 20° C. ($\eta_{20}$) was 27.2 mPa·s. Assuming this liquid crystal composition as mother liquid crystal (hereinafter referred to as Mother liquid crystal A), 15% of the 4-(trans-4-(3-butenyl)cyclohexyl)-4'-ethyltolan (Compound No. 45) described in Example 1 was mixed with 85% of Mother liquid crystal A, and physical properties of the mixture were determined. As the result, it was found that $T_{NI}$ was 88.3° C., $V_{th}$ was 1.89 V, $\Delta\epsilon$ was 10.4, $\Delta n$ was 0.155, and $\eta_{20}$ was 25.2 mPa·s. Whereas this liquid crystal composition was left in a freezer at −20° C. for 20 days, neither precipitation of crystals nor development of smectic phase was observed.

EXAMPLE 10 (Use Example 2)

To 85% of Mother liquid crystal composition A described in Example 9 was mixed 15% of the 4-(trans-4-(3-butenyl)cyclohexyl)-2,6-difluoro-4'-ethyltolan (Compound No. 56) described in Example 2, and physical properties of the mixture were determined. As the result, it was found that $T_{NI}$ was 83.0° C., $V_{th}$ was 1.86 V, $\Delta\epsilon$ was 10.3, $\Delta n$ was 0.154, and $\eta_{20}$ was 26.1 mPa·s.

EXAMPLE 11 (Use Example 3)

To 85% of Mother liquid crystal composition A described in Example 9 was mixed 15% of 4-(3-butenyl)-4'-pentyltolan (Compound No. 7), and physical properties of the mixture were determined. As the result, it was found that $T_{NI}$ was 67.1° C., $V_{th}$ was 1.72 V, $\Delta\epsilon$ was 10.2, $\Delta n$ was 0.150, and $\eta_{20}$ was 21.6 mPa·s.

EXAMPLE 12 (Use Example 4)

To 85% of Mother liquid crystal composition A described in Example 9 was mixed 15% of 4-(3-butenyl)-4'-heptoxytolan (Compound No. 12-1), and physical properties of the mixture were determined. As the result, it was found that $T_{NI}$ was 66.7° C., $V_{th}$ was 1.59 V, $\Delta\epsilon$ was 9.8, $\Delta n$ was 0.144, and $\eta_{20}$ was 25.4 mPa·s.

EXAMPLE 13 (Use Example 5)

To 85% of Mother liquid crystal composition A described in Example 9 was mixed 15% of 4-(3-butenyl)-4'-(trans-4-pentylcyclohexyl)tolan (Compound No. 258-1), and physical properties of the mixture were determined. As the result, it was found that $T_{NI}$ was 87.5° C., $V_{th}$ was 1.82 V, $\Delta\in$ was 10.3, $\Delta n$ was 0.153, and $\eta_{20}$ was 25.9 mPa·s.

Whereas the liquid crystal compositions of these Examples 10 to 13 were left in a freezer at −20° C. for 20 days, respectively, neither precipitation of crystals nor development of smectic phase was observed.

In the same manner, the following liquid crystal compositions were prepared and their physical properties were determined. (In the followings, the meaning of abbreviation is the same as described above. Also, in the following, $\eta_{20}$ is abbreviated as $\eta$.)

EXAMPLE 14 (Use Example 6)

| | |
|---|---|
| V2-BTB-5 | 5.0% |
| V2-BTB-O7 | 5.0% |
| 1V2-BEB(F,F)—C | 5.0% |
| 3-HB-C | 25.0% |
| 1-BTB-3 | 5.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

$T_{NI}$=93.5 (° C.)
$\eta$=16.6 (mPa·s)
$\Delta n$=0.159
$\Delta\in$=7.2
$V_{th}$=2.02 (V)

EXAMPLE 15 (Use Example 7)

| | |
|---|---|
| V2-BTBH-5 | 4.0% |
| 2O1-BEB(F)—C | 5.0% |
| 3O1-BEB(F)—C | 15.0% |
| 4O1-BEB(F)—C | 13.0% |
| 5O1-BEB(F)—C | 13.0% |
| 2-HHB(F)—C | 15.0% |
| 3-HHB(F)—C | 15.0% |
| 3-HB(F)TB-2 | 4.0% |
| 3-HB(F)TB-3 | 4.0% |
| 3-HB(F)TB-4 | 4.0% |
| 3-HHB-1 | 4.0% |
| 3-HHB-O1 | 4.0% |

$T_{NI}$=92.1 (° C.)
$\eta$=86.1 (mPa·s)
$\Delta n$=0.155
$\Delta\in$=31.1
$V_{th}$=0.86 (V)

EXAMPLE 16 (Use Example 8)

| | |
|---|---|
| V2-BTB-5 | 4.0% |
| V2-BTB-O7 | 5.0% |
| V2-BTBH-5 | 4.0% |
| 5-PyB-F | 4.0% |
| 3-PyB(F)—F | 4.0% |
| 2-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 4.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

$T_{NI}$=96.5 (° C.)
$\eta$=33.7 (mPa·s)
$\Delta n$=0.208
$\Delta\in$=5.9
$V_{th}$=2.68 (V)

EXAMPLE 17 (Use Example 9)

| | |
|---|---|
| V2-BTB-5 | 5.0% |
| V2-HBTB-2 | 3.0% |
| 3-GB-C | 10.0% |
| 4-GB-C | 10.0% |
| 2-BEB-C | 12.0% |
| 3-BEB-C | 4.0% |
| 3-PyB(F)—F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 1O-BEB-2 | 4.0% |
| 3-HHB-1 | 3.0% |
| 3-HHEBB-C | 3.0% |
| 3-HBEBB-C | 3.0% |
| 5-HBEBB-C | 3.0% |

$T_{NI}$=70.6 (° C.)
$\eta$=38.4 (mPa·s)
$\Delta n$=0.135
$\Delta\in$=11.8
$V_{th}$=1.19 (V)

EXAMPLE 18 (Use Example 10)

| | |
|---|---|
| V2-BTB-O7 | 3.0% |
| V2-HB(F,F)TB-2 | 4.0% |
| 3-HB-C | 18.0% |
| 1O1-HB-C | 10.0% |
| 3-HB(F)—C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 4.0% |
| 3-H2BTB-2 | 3.0% |
| 3-H2BTB-3 | 3.0% |
| 2-PyBH-3 | 4.0% |

-continued

| | |
|---|---|
| 3-PyBH-3 | 3.0% |
| 3-PyBB-2 | 3.0% |

$T_{NI}$=78.7 (° C.)
η=18.1 (mPa·s)
Δn=0.148
Δ∈=8.1
$V_{th}$=1.75 (V)

EXAMPLE 19 (Use Example 11)

| | |
|---|---|
| V2-HBTB-2 | 4.0% |
| V2-HB(F,F)TB-2 | 4.0% |
| 2O1-BEB(F)—C | 5.0% |
| 3O1-BEB(F)—C | 12.0% |
| 5O1-BEB(F)—C | 4.0% |
| 1V2-BEB(F,F)—C | 10.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB(F)—C | 2.0% |
| 3-HB(F)EB(F)—C | 2.0% |
| 3-HBEB(F,F)—C | 2.0% |
| 3-HHB-F | 4.0% |
| 3-HHB-O1 | 4.0% |
| 3-HHB-3 | 5.0% |
| 3-HEBEB-F | 2.0% |
| 3-HEBEB-1 | 2.0% |

$T_{NI}$=78.1 (° C.)
η=35.7 (mPa·s)
Δn=0.127
Δ∈=24.0
$V_{th}$=0.82 (V)

EXAMPLE 20 (Use Example 12)

| | |
|---|---|
| V2-BTB-5 | 5.0% |
| V2-HBTB-2 | 7.0% |
| 2-HHB(F)—F | 17.0% |
| 3-HHB(F)—F | 17.0% |
| 5-HHB(F)—F | 16.0% |
| 2-H2HB(F)—F | 10.0% |
| 5-H2HB(F)—F | 10.0% |
| 2-HBB(F)—F | 6.0% |
| 3-HBB(F)—F | 6.0% |
| 5-HBB(F)—F | 6.0% |

$T_{NI}$=103.9 (° C.)
η=22.6 (mPa·s)
Δn=0.112
Δ∈=5.0
=$V_{th}$=2.27 (V)

EXAMPLE 21 (Use Example)

| | |
|---|---|
| V2-HB(F,F)TB-2 | 7.0% |
| V2-BTB-O7 | 3.0% |
| 7-HB(F,F)—F | 3.0% |
| 3-HB-O2 | 7.0% |
| 2-HHB(F)—F | 10.0% |

-continued

| | |
|---|---|
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 9.0% |
| 2-HBB-F | 4.0% |
| 3-HBB-F | 4.0% |
| 3-HBB(F,F)—F | 5.0% |
| 5-HBB(F,F)—F | 10.0% |

$T_{NI}$=86.5 (° C.)
η=24.6 (mPa·s)
Δn=0.124
Δ∈=5.6
$V_{th}$=2.14 (V)

EXAMPLE 22 (Use Examle 14)

| | |
|---|---|
| V2-BTB-5 | 4.0% |
| V2-BTB-O7 | 4.0% |
| 3-HB-CL | 10.0% |
| 1O1-HH-5 | 5.0% |
| 2-HBB(F)—F | 8.0% |
| 3-HBB(F)—F | 8.0% |
| 5-HBB(F)—F | 14.0% |
| 4-HHB-CL | 8.0% |
| 5-HHB-CL | 8.0% |
| 3-H2HB(F)—CL | 4.0% |
| 3-HBB(F,F)—F | 10.0% |
| 5-H2BB (F,F)—F | 9.0% |
| 3-HB(F)VB-2 | 4.0% |
| 3-HB(F)VB-3 | 4.0% |

$T_{NI}$=94.1 (° C.)
η=21.6 (mPa·s)
Δn=0.140
Δ∈=4.8
$V_{th}$=2.41 (V)

EXAMPLE 23 (Use Example 15)

| | |
|---|---|
| V2-BTB-5 | 7.0% |
| V2-BTB-O7 | 7.0% |
| V2-BTBH-5 | 7.0% |
| 3-HHB(F,F)—F | 9.0% |
| 3-H2HB(F,F)—F | 8.0% |
| 4-H2HB(F,F)—F | 8.0% |
| 5-H2HB(F,F)—F | 8.0% |
| 5-HBB(F,F)—F | 20.0% |
| 3-H2BB(F,F)—F | 10.0% |
| 5-HHBB(F,F)—F | 3.0% |
| 5-HHEBB-F | 2.0% |
| 3-HH2BB(F,F)—F | 3.0% |
| 1O1-HBBH-4 | 4.0% |
| 1O1-HBBH-5 | 4.0% |

$T_{NI}$=105.5 (° C.)
η=29.9 (mPa·s)
Δn=0.137
Δ∈=7.6
$V_{th}$=2.46 (V)

EXAMPLE 24 (Use Example 16)

| | |
|---|---|
| V2-BTB-O7 | 5.0% |
| V2-BTBH-5 | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)—OCF3 | 5.0% |
| 3-HBB(F)—F | 10.0% |
| 3-HH2B(F)—F | 3.0% |
| 3-HB(F)BH-3 | 3.0% |
| 5-HBBH-3 | 3.0% |
| 3-HHB(F,F)—OCF2H | 4.0% |

$T_{NI}$=87.0 (° C.)
η=14.1 (mPa·s)
Δn=0.100
Δ∈=4.1
$V_{th}$=2.78 (V)

EXAMPLE 25 (Use Example 17)

| | |
|---|---|
| V2-HBTB-2 | 5.0% |
| V2-HB(F,F)TB-2 | 5.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 1O1-HBBH-4 | 5.0% |
| 1O1-HBBH-5 | 5.0% |

$T_{NI}$=103.4 (° C.)
η=34.4 (mPa·s)
Δn=0.147
Δ∈=7.1
$V_{th}$=2.09 (V)

EXAMPLE 26 (Use Example 18)

| | |
|---|---|
| V2-BTB-5 | 5.0% |
| V2-HBTB-2 | 5.0% |
| V2-HB(F,F)TB-2 | 5.0% |
| 3-H2HB(F,F)—F | 7.0% |
| 5-H2HB(F,F)—F | 8.0% |
| 3-HHB(F,F)—F | 10.0% |
| 4-HHB(F,F)—F | 5.0% |
| 3-HH2B(F,F)—F | 9.0% |
| 5-HH2B(F,F)—F | 9.0% |
| 5-HHB(F,F)—F | 15.0% |
| 3-HBEB(F,F)—F | 2.0% |
| 4-HBEB(F,F)—F | 2.0% |
| 5-HBEB(F,F)—F | 2.0% |
| 3-HHEB(F,F)—F | 10.0% |
| 4-HHEB(F,F)—F | 3.0% |
| 5-HHEB(F,F)—F | 3.0% |

$T_{NI}$=92.5 (° C.)
η=28.2 (mPa·s)
Δn=0.111
Δ∈=10.5
$V_{th}$=2.21 (V)

COMPARATIVE EXAMPLE 1

As a compound to be compared to the compounds of the present invention, the compound (23) described in Mol. Cryst. Liq. Cryst., vol. 141, p 279 (1986) was actually synthesized, and assumed to be comparative compound.

Liquid crystal composition in which 85% of Mother liquid crystal A described above and 15% of the comparative compound (23) were mixed was prepared, and its optical anisotropy (Δn; extrapolation value) was determined. Its result, and phase transition temperatures and miscibility of the compound are shown in Table 2 together with the results of Examples 9 and 10.

TABLE 2

| | Phase transition temperature (° C.) | Δn[a)] | Miscibility[b)] |
|---|---|---|---|
| 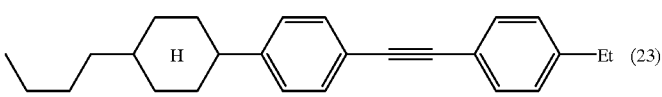 (23) | C.102.N.197.I | 0.249 | 7 |
| 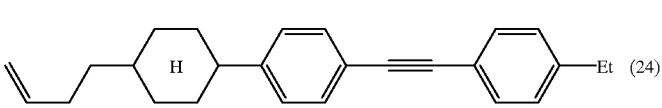 (24) (Compound No. 49) | C.58.9.S.115.1.N.175.I | 0.257 | >20 |

TABLE 2-continued

| | Phase transition temperature (° C.) | Δn[a] | Miscibility[b] |
|---|---|---|---|
| 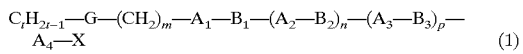 (Compound No. 56) | C.75.1.N.174.6.I | 0.250 | >20 |

[a]Extrapolatied value
[b]Number of days passed by the time when precipitation of crystals or appearance of smectic phase was confirmed after initiation of leaving of the compound in a freezer at −20° C.

As shown in Table 2, whereas the comparative compound (23) had a transition temperature from crystal to liquid crystal phase of 102° C., compounds (24) and (25) had a phase transition temperature of 58.9° C. and 75.1° C., respectively. With respect to the temperature range of liquid crystal phase, whereas the range of the compound (23) was 95° C., that of compounds (24) and (25) were 116° C. and 100° C., respectively. As will be seen from these results, the compounds of the present invention are remarkably low in the lower temperature limit for exhibiting liquid crystal phase and wide in the temperature range compared with conventional liquid crystalline compounds. Accordingly, liquid crystal compositions comprising the compound of the present invention can be considered to have wide range of liquid crystal display in practical use. As shown in Table 2, the value of optical anisotropy of the compounds of the present invention were also higher than that of conventional liquid crystalline compounds. Accordingly, it is possible to reduce the thickness of liquid crystal cells and increase the response speed in cells by using liquid crystal compositions comprising the compound of the present invention. Besides, whereas solids exhibiting smectic phase were precipitated in 7 days when the compound (23) was left in a freezer at −20° C., precipitation of crystals or the likes was not caused in 20 days or more with respect to the compounds (24) and (25) of the present invention to confirm that the compounds of the present invention have remarkably excellent miscibility at low temperatures. As described above, the compounds of the present invention have characteristics which can not be found in known liquid crystal compounds, and have excellent properties as liquid crystal material.

INDUSTRIAL APPLICABILITY

As described above, according to the present invention, (a) tolan derivatives, novel liquid crystalline compounds having sufficiently high optical anisotropy, high dielectric anisotropy, large ratio of elastic constants, excellent miscibility with other liquid crystalline compounds, low viscosity, and chemical and physical stability; (b) liquid crystal compositions comprising the tolan derivative; and (c) liquid crystal display devices including the liquid crystal composition can be provided.

What is claimed is:

1. A liquid crystalline alkenyltolan derivative expressed by the general formula (1)

$$C_tH_{2t-1}-G-(CH_2)_m-A_1-B_1-(A_2-B_2)_n-(A_3-B_3)_p-A_4-X \quad (1)$$

wherein $A_1$, $A_2$, $A_3$, and $A_4$ independently represent a 1,4-cyclohexylene, 1,4-phenylene in which one or two hydrogen atoms may be replaced by a fluorine atom(s), dioxane-2,5-diyl, or pyrimidine-2,5-diyl group; $B_1$, $B_2$, and $B_3$ independently represent a covalent bond, an 1,2-ethylene, 1,2-ethenylene, 1,2-ethynylene, oxymethylene, methylenoxy or carbonyloxy provided that at least one of $B_1$, $B_2$, and $B_3$ represents an 1,2-ethynylene group; G represents a covalent bond or an oxygen atom; $C_tH_{2t-1}$ represents an alkenyl group having t carbon atoms wherein t is an integer of 2 to 10; m is an integer of 0 to 2; n and p are independently an integer of 0 or 1; X represents an alkyl group having 1 to 10 carbon atoms, a fluoroalkyl group having 1 to 10 carbon atoms, a chlorine atom, a bromine atom, or a cyano group wherein one or more methylene groups or fluoromethylene groups in the alkyl group or the fluoroalkyl group may be replaced by an oxygen atom(s) or an 1,2-ethenylene group, but adjacent two methylene groups should not be simultaneously replaced by them; provided that when $A_4$ represents 1,4-phenylene group which is not substituted with a fluorine atom(s), there is no case that G represents a covalent bond and t+m=3 simultaneously; provided that when $A_1$ represents 1,4-phenylene group which is not substituted with a fluorine atom(s), $B_1$ represents 1,2-ethynylene, and G represents a covalent bond, there is no case that t+m=3; provided that when $A_1$ represents a 1,4-phenylene group wherein fluorine atoms replace two hydrogens and $A_4$ represents a 1,4-cyclohexane, $B_1$ is not a triple covalent bond; and each element in the molecule may be its isotope.

2. The liquid crystalline alkenyltolan derivative according to claim 1 wherein n and p are 0.

3. The liquid crystalline alkenyltolan derivative according to claim 1 wherein n is 1 and p is 0.

4. The liquid crystalline alkenyltolan derivative according to claim 1 wherein n and p are 1.

5. The liquid crystalline alkenyltolan derivative according to claim 2 wherein X represents a chlorine atom, a bromine atom, a cyano group, or a fluoroalkyl group having 1 to 10 carbon atoms in which one or more fluoromethylene groups may be replaced by an oxygen atom(s) or an 1,2-ethenylene group(s).

6. The liquid crystalline alkenyltolan derivative according to claim 2 wherein X represents an alkyl group having 1 to 10 carbon atoms in which one or more methylene groups may be replaced by an oxygen atom(s) or an 1,2-ethenylene group(s); and $A_1$ and $A_4$ independently represent a 1,4-phenylene group in which one or two hydrogen atoms may be replaced by a fluorine atom(s).

7. The liquid crystalline alkenyltolan derivative according to claim 2 wherein G represents a covalent bond, t+m=4, and a double bond exists at a terminal of the molecule.

8. The liquid crystalline alkenyltolan derivative according to claim 2 wherein G represents a covalent bond, t+m=5, and a double bond exists at a second position counting from a terminal of the molecule.

9. The liquid crystalline alkenyltolan derivative according to claim 3 wherein X represents a chlorine atom, a bromine atom, a cyano group, or a fluoroalkyl group having 1 to 10 carbon atoms in which one or more fluoromethylene groups may be replaced by an oxygen atom(s) or an 1,2-ethenylene group(s).

10. The liquid crystalline alkenyltolan derivative according to claim 3 wherein X represents an alkyl group having 1 to 10 carbon atoms in which one or more methylene groups may be replaced by an oxygen atom(s) or an 1,2-ethenylene group(s).

11. The liquid crystalline alkenyltolan derivative according to claim 10 wherein G represents a covalent bond, t+m=4, and a double bond exists at a terminal of the molecule.

12. The liquid crystalline alkenyltolan derivative according to claim 10 wherein G represents a covalent bond, t+m=5, and a double bond exists at a second position counting from a terminal of the molecule.

13. The liquid crystalline alkenyltolan derivative according to claim 11 wherein $B_1$ represents a covalent bond and $B_2$ represents an 1,2-ethynylene group.

14. The liquid crystalline alkenyltolan derivative according to claim 12 wherein $B_1$ represents a covalent bond and $B_2$ represents an 1,2-ethynylene group.

15. The liquid crystalline alkenyltolan derivative according to claim 13 wherein $A_1$ represents an 1,4-cyclohexylene group, and $A_2$ and/or $A_4$ represents an 1,4-phenylene group in which a hydrogen atom(s) may be replaced by a fluorine atom(s).

16. The liquid crystalline alkenyltolan derivative according to claim 15 wherein $A_2$ and $A_4$ represent 1,4-phenylene group in which a hydrogen atom(s) is not replaced by a fluorine atom(s).

17. The liquid crystalline alkenyltolan derivative according to claim 15 wherein $A_2$ represents 1,4-phenylene group in which two hydrogen atoms are replaced by fluorine atoms and $A_4$ represents 1,4-phenylene group in which a hydrogen atom(s) is not replaced by a fluorine atom(s).

18. The liquid crystalline alkenyltolan derivative according to claim 3 wherein G represents a covalent bond, t+m=4, and a double bond exists at a terminal of the molecule.

19. The liquid crystalline alkenyltolan derivative according to claim 3 wherein G represents a covalent bond, t+m=5, and a double bond exists at a second position counting from a terminal of the molecule.

20. The liquid crystalline alkenyltolan derivative according to claim 4 wherein X represents a chlorine atom, a bromine atom, a cyano group, or a fluoroalkyl group having 1 to 10 carbon atoms in which one or more fluoromethylene groups may be replaced by an oxygen atom(s) or an 1,2-ethenylene group(s).

21. The liquid crystalline alkenyltolan derivative according to claim 4 wherein X represents an alkyl group having 1 to 10 carbon atoms in which one or more methylene groups may be replaced by an oxygen atom(s) or an 1,2-ethenylene group(s).

22. The liquid crystalline alkenyltolan derivative according to claim 21 wherein $A_2$ and/or $A_4$ represents 1,4-phenylene group in which one or two hydrogen atoms may be replaced by an fluorine atom(s) and $B_3$ represents 1,2-ehtynylene group.

23. The liquid crystalline alkenyltolan derivative according to claim 21 wherein $A_2$ and/or $A_3$ represents an 1,4-phenylene group in which one or two hydrogen atoms may be replaced by an fluorine atom(s) and $B_2$ represents an 1,2-ehtynylene group.

24. The liquid crystalline alkenyltolan derivative according to claim 23 wherein one or two hydrogen atoms of $A_2$ and/or $A_3$ are replaced by an fluorine atom(s).

25. The liquid crystalline alkenyltolan derivative according to claim 4 wherein G represents a covalent bond, t+m=4, and a double bond exists at a terminal of the molecule.

26. The liquid crystalline alkenyltolan derivative according to claim 4 wherein G represents a covalent bond, t+m=5, and a double bond exists at a second position counting from a terminal of the molecule.

27. A liquid crystal composition comprising at least two components and comprising at least one liquid crystalline compound defined in claim 1.

28. A liquid crystal composition comprising, as a first component, at least one liquid crystalline compound defined in claim 1, and comprising, as a second component, at least one compound selected from the group consisting of the compounds expressed by any one of the general formulas (2), (3), and (4)

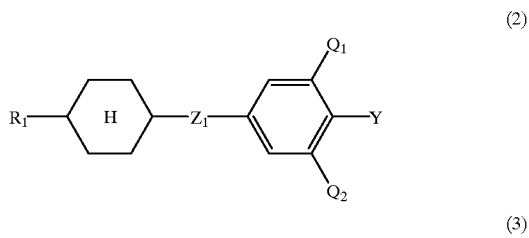

(2)

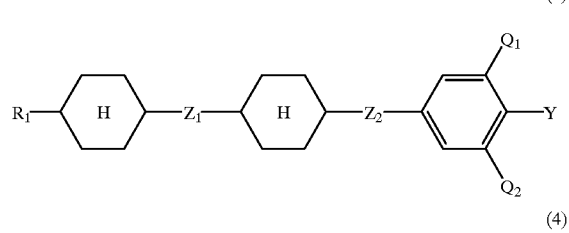

(3)

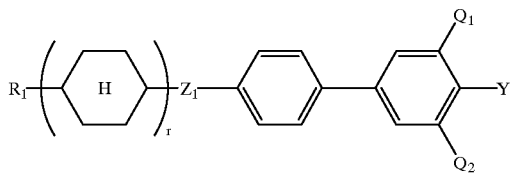

(4)

wherein $R_1$ represents an alkyl group or alkyloxy group having 1 to 10 carbon atoms; Y represents a fluorine atom or a chlorine atom; $Q_1$ and $Q_2$ independently represent a hydrogen atom or a fluorine atom; r is 1 or 2; and $Z_1$ and $Z_2$ independently represent a covalent bond or —$CH_2CH_2$—.

29. A liquid crystal composition comprising, as a first component, at least one compound defined in claim 1, and comprising, as a second component, at least one compound selected from the group consisting of the compounds expressed by any one of the general formulas (5), (6), (7), (8), and (9)

(5)

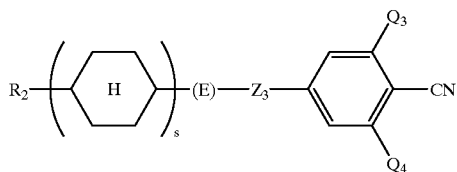

(6)

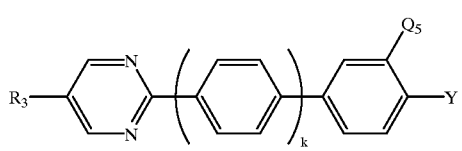

(7)

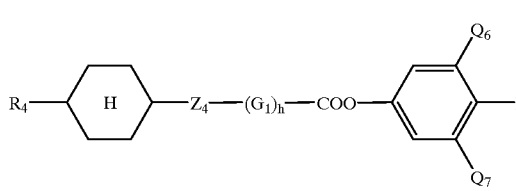

(8)

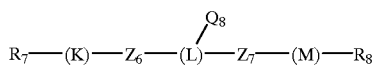

(9)

R$_7$—(K)—Z$_6$—(L)$\overset{Q_8}{\diagup}$—Z$_7$—(M)—R$_8$ wherein R$_2$ represents an alkyl group having 1 to 10 carbon atoms or an alkenyl group having 2 to 10 carbon atoms, and any methylene group (—CH$_2$—) in the alkyl or the alkenyl group may be replaced by an oxygen atom (—O—), but adjacent two or more methylene groups are not replaced by an oxygen atom(s) simultaneously; Z$_3$ represents a covalent bond, —CH$_2$CH$_2$—, or —COO—; Q$_3$ and Q$_4$ independently represent a hydrogen atom or a fluorine atom; (E) represents an 1,4-cyclohexylene, 1,4-phenylene, or dioxane-2,5-diyl group; s is 0 or 1; R$_3$ represents an alkyl group having 1 to 10 carbon atoms; Q$_5$ represents a hydrogen atom or a fluorine atom; k is 0 or 1; R$_4$ represents an alkyl group having 1 to 10 carbon atoms; (G$_1$) represents an 1,4-cyclohexylene or 1,4-phenylene group; Q$_6$ and Q$_7$ independently represent a hydrogen atom or a fluorine atom; Z$_4$ represents a covalent bond or —COO—; h is 0 or 1; R$_5$ and R$_6$ independently represent an alkyl group, alkyloxy group, or alkyloxymethyl group, each having 1 to 10 carbon atoms; (H) represents an 1,4-cyclohexylene, pyrimidine-2,5-diyl, or 1,4-phenylene group; (J) represents an 1,4-cyclohexylene or 1,4-phenylene group; Z$_5$ represents a covalent bond, —CH$_2$CH$_2$—, —C≡C—, or —COO—; R$_7$ represents an alkyl group or alkyloxy group, each having 1 to 10 carbon atoms; R$_8$ represents an alkyl group, alkyloxy group, or alkyloxymethyl group, each having 1 to 10 carbon atoms; (K) represents an 1,4-cyclohexylene or pyrimidine-2,5-diyl group; (L) and (M) independently represent an 1,4-cyclohexylene or 1,4-phenylene group; Z$_6$ represents a covalent bond, —CH$_2$CH$_2$—, or —COO—; Z$_7$ represents a covalent bond, —C≡C—, or —COO—; and Q$_8$ represents a hydrogen atom or a fluorine atom.

30. A liquid crystal display device including a liquid crystal composition comprising at least 2 components and comprising at least one liquid crystalline compound defined in claim 1.

31. A liquid crystal display device including a liquid crystal composition defined in claim 28.

32. A liquid crystal display device including a liquid crystal composition defined in claim 29.

* * * * *